United States Patent
Brown, Jr. et al.

(10) Patent No.: US 8,578,544 B2
(45) Date of Patent: Nov. 12, 2013

(54) ORAL HYGIENE IMPLEMENTS HAVING FLEXIBLE ELEMENTS, AND METHODS OF MAKING THE SAME

(75) Inventors: William Ralph Brown, Jr., Peabody, MA (US); Karen Lynn Claire-Zimmet, Waltham, MA (US); Soeren Jan Wasow, Freigericht (DE); Steffi Raehse, Eschborn (DE); Tilmann Winkler, Kronberg (DE)

(73) Assignee: The Gillette Company, Boston, MA (US)

( * ) Notice: Subject to any disclaimer, the term of this patent is extended or adjusted under 35 U.S.C. 154(b) by 1478 days.

(21) Appl. No.: 12/012,067

(22) Filed: Jan. 31, 2008

(65) Prior Publication Data

US 2008/0184511 A1 Aug. 7, 2008

Related U.S. Application Data

(60) Provisional application No. 60/899,051, filed on Feb. 2, 2007, provisional application No. 60/928,711, filed on May 11, 2007.

(51) Int. Cl.
- A46B 9/04 (2006.01)
- A46D 1/00 (2006.01)
- A61H 7/00 (2006.01)

(52) U.S. Cl.
USPC ............. 15/110; 15/201; 15/206; 15/167.1; 15/104.94

(58) Field of Classification Search
USPC ............................................ 15/110

IPC .................. A46B 9/04; A46D 1/00; A61H 7/00
See application file for complete search history.

(56) References Cited

U.S. PATENT DOCUMENTS

| | | |
|---|---|---|
| 759,490 A | 5/1904 | Yates |
| 1,327,807 A | 1/1920 | Burleigh |
| 1,369,664 A | 2/1921 | Izawa |
| 1,466,723 A | 9/1923 | Izawa |
| 1,693,229 A | 11/1928 | Felmar |
| 1,927,365 A | 9/1933 | Frolio |
| 1,976,271 A | 10/1934 | Vachoux |
| 2,003,243 A | 5/1935 | Campbell et al. |

(Continued)

FOREIGN PATENT DOCUMENTS

| | | |
|---|---|---|
| CA | 1 248 307 | 1/1989 |
| DE | 102006024874 A1 | 11/2007 |

(Continued)

OTHER PUBLICATIONS

Jan. 31, 2008, European Search Report.

*Primary Examiner* — Monica Carter
*Assistant Examiner* — Stephanie Berry
(74) *Attorney, Agent, or Firm* — James E. Oehlenschlager; George Henry Leal

(57) ABSTRACT

An oral hygiene implement includes a cleaning element carrier and a body. The body has a proximal end and a distal end. The cleaning element carrier has a first area and a second area wherein the second area is disposed inboard of the first area. The first area is attached to the body while the second area is unattached to the body. A bending element is disposed between the first area and the second area, thereby allowing the second area to bend/flex while the first area stays fixed to the body.

20 Claims, 29 Drawing Sheets

(56) References Cited

U.S. PATENT DOCUMENTS

| | | |
|---|---|---|
| 2,022,039 A | 11/1935 | House |
| 2,221,363 A | 11/1940 | Sweatt |
| 2,244,098 A | 6/1941 | Busick |
| 2,254,365 A | 9/1941 | Griffith et al. |
| 2,266,195 A * | 12/1941 | Hallock ............... 15/167.1 |
| 2,438,268 A | 3/1948 | Bressler |
| 2,433,297 A | 6/1948 | Bressler |
| 2,474,684 A | 6/1949 | McCaughley |
| 2,631,320 A | 3/1953 | Bressler |
| 2,650,383 A | 9/1953 | Bressler |
| 2,676,350 A | 4/1954 | Bressler |
| 2,685,703 A | 8/1954 | Dellenbach |
| 2,749,567 A | 6/1956 | Krueger |
| 2,807,820 A | 10/1957 | Dinhofer |
| 2,864,111 A | 12/1958 | Rotceig |
| 2,971,518 A | 2/1961 | O'Neal |
| 3,152,349 A | 10/1964 | Brennesholtz |
| 3,188,672 A | 6/1965 | Gary |
| 3,193,864 A | 7/1965 | Makowsky |
| 3,493,991 A | 2/1970 | De Bianchi |
| 3,847,662 A | 11/1974 | Massa |
| D248,696 S | 8/1978 | Greenberg |
| 4,330,896 A | 5/1982 | Booth |
| 4,356,585 A | 11/1982 | Protell et al. |
| 4,520,526 A | 6/1985 | Peters |
| 4,638,521 A | 1/1987 | Potente et al. |
| 4,691,405 A | 9/1987 | Reed |
| 4,693,622 A | 9/1987 | Booth |
| 4,757,570 A | 7/1988 | Haeusser et al. |
| 4,776,054 A | 10/1988 | Rauch |
| 4,783,874 A | 11/1988 | Perches et al. |
| 4,796,325 A | 1/1989 | Bortman |
| 4,829,621 A | 5/1989 | Phenegar |
| 4,864,676 A | 9/1989 | Schaiper |
| 5,001,803 A | 3/1991 | Discko, Jr. |
| 5,033,154 A | 7/1991 | Marchand et al. |
| 5,052,071 A | 10/1991 | Halm |
| 5,054,154 A | 10/1991 | Schiffer et al. |
| 5,121,520 A | 6/1992 | Brice |
| 5,315,732 A | 5/1994 | Huefner et al. |
| 5,323,504 A | 6/1994 | McCusker |
| 5,373,602 A | 12/1994 | Bang |
| 5,465,450 A | 11/1995 | Humphries |
| 5,481,775 A | 1/1996 | Gentile et al. |
| 5,483,722 A | 1/1996 | Scheier et al. |
| 5,499,421 A | 3/1996 | Brice |
| 5,581,838 A | 12/1996 | Rocco |
| 5,628,082 A | 5/1997 | Moskovich |
| 5,630,244 A | 5/1997 | Chang |
| 5,651,158 A | 7/1997 | Halm |
| 5,673,452 A | 10/1997 | Chang et al. |
| 5,673,453 A | 10/1997 | Huang |
| 5,678,273 A | 10/1997 | Porcelli |
| 5,692,260 A | 12/1997 | Haiduk |
| 5,707,166 A | 1/1998 | Jeannet et al. |
| 5,735,012 A | 4/1998 | Heinzelman et al. |
| 5,749,381 A | 5/1998 | Butler et al. |
| 5,758,383 A | 6/1998 | Hohlbein |
| 5,765,254 A | 6/1998 | O'Halloran |
| 5,802,656 A | 9/1998 | Dawson et al. |
| 5,815,875 A | 10/1998 | Yamada |
| 5,850,659 A | 12/1998 | Butler et al. |
| 5,863,102 A | 1/1999 | Waguespack et al. |
| 5,898,967 A | 5/1999 | Wu et al. |
| 5,915,868 A | 6/1999 | Frazell |
| 5,946,758 A | 9/1999 | Hohlbein et al. |
| 5,946,759 A | 9/1999 | Cann |
| 5,956,797 A | 9/1999 | Wilson |
| RE36,407 E | 11/1999 | Rocco |
| 5,987,690 A | 11/1999 | Heuler |
| 5,991,958 A | 11/1999 | Hohlbein |
| 5,991,959 A | 11/1999 | Raven et al. |
| 6,003,189 A | 12/1999 | Falleiros |
| 6,073,299 A | 6/2000 | Hohlbein |
| 6,088,870 A | 7/2000 | Hohlbein |
| 6,112,361 A | 9/2000 | Brice |
| 6,115,870 A | 9/2000 | Solanki et al. |
| 6,178,582 B1 | 1/2001 | Halm |
| 6,182,321 B1 | 2/2001 | Wu |
| 6,219,874 B1 | 4/2001 | Van Gelder et al. |
| 6,254,390 B1 | 7/2001 | Wagner |
| 6,295,686 B1 | 10/2001 | Phillips |
| 6,301,814 B1 | 10/2001 | Baxter |
| 6,314,605 B1 | 11/2001 | Solanki et al. |
| 6,314,606 B1 | 11/2001 | Hohlbein |
| 6,327,735 B1 | 12/2001 | Kramer |
| 6,357,073 B1 | 3/2002 | Yue |
| 6,357,074 B1 | 3/2002 | Weihrauch |
| D456,139 S | 4/2002 | Hohlbein |
| 6,385,808 B1 | 5/2002 | Yamada et al. |
| 6,405,401 B1 | 6/2002 | Hellerud et al. |
| 6,408,473 B1 | 6/2002 | Kessler |
| 6,408,476 B1 | 6/2002 | Cann |
| D463,133 S | 9/2002 | Hohlbein |
| 6,442,786 B2 | 9/2002 | Halm et al. |
| 6,442,787 B2 | 9/2002 | Hohlbein |
| 6,453,501 B1 | 9/2002 | Bella |
| 6,505,373 B2 | 1/2003 | Van Gelder et al. |
| 6,510,575 B2 | 1/2003 | Calabrese |
| 6,514,445 B1 | 2/2003 | Cann et al. |
| 6,550,095 B2 | 4/2003 | Hawkins et al. |
| 6,564,416 B1 | 5/2003 | Claire et al. |
| 6,611,984 B1 | 9/2003 | Halm |
| 6,643,886 B2 | 11/2003 | Moskovich et al. |
| 6,668,416 B1 | 12/2003 | Georgi et al. |
| 6,675,428 B2 | 1/2004 | Halm |
| 6,700,230 B1 | 3/2004 | Gokturk |
| 6,708,364 B1 | 3/2004 | Huber |
| RE38,521 E | 5/2004 | Halm |
| 6,807,703 B2 | 10/2004 | Van Gelder et al. |
| 6,810,551 B1 | 11/2004 | Weihrauch |
| 6,883,200 B1 | 4/2005 | Euler |
| 6,948,209 B2 | 9/2005 | Chan |
| 6,988,777 B2 | 1/2006 | Pfenniger et al. |
| 6,996,870 B2 | 2/2006 | Hohlbein |
| 7,007,332 B2 | 3/2006 | Hohlbein |
| 7,020,928 B2 * | 4/2006 | Hohlbein ............... 15/167.1 |
| 7,024,720 B2 | 4/2006 | Moskovich et al. |
| 7,059,471 B2 | 6/2006 | Fattori |
| 7,162,767 B2 | 1/2007 | Pfenniger et al. |
| 7,219,384 B2 | 5/2007 | Hohlbein |
| 7,226,555 B2 | 6/2007 | Weihrauch |
| 7,275,277 B2 | 10/2007 | Moskovich et al. |
| 7,281,289 B1 | 10/2007 | Mirza et al. |
| 7,334,286 B2 | 2/2008 | Kayser |
| 7,360,270 B2 | 4/2008 | Moskovich et al. |
| 7,363,823 B2 | 4/2008 | Brice |
| 7,386,909 B2 | 6/2008 | Hohlbein |
| 7,430,776 B2 | 10/2008 | Eliav |
| 7,430,780 B2 | 10/2008 | Moskovich et al. |
| 7,475,775 B2 | 1/2009 | Fattori |
| 7,503,093 B2 | 3/2009 | Weihrauch |
| 7,546,658 B2 | 6/2009 | Koeth et al. |
| 7,549,187 B2 | 6/2009 | Pfenniger et al. |
| 2001/0014991 A1 | 8/2001 | Halm et al. |
| 2002/0017003 A1 | 2/2002 | Kramer et al. |
| 2002/0138931 A1 | 10/2002 | Davies |
| 2003/0009837 A1 | 1/2003 | Cann |
| 2003/0135944 A1 | 7/2003 | Brice |
| 2004/0006837 A1 | 1/2004 | Cann |
| 2004/0045204 A1 | 3/2004 | Miano et al. |
| 2004/0047013 A1 | 3/2004 | Cai et al. |
| 2004/0121284 A1 | 6/2004 | Hsu |
| 2004/0177462 A1 | 9/2004 | Brown, Jr. et al. |
| 2005/0091767 A1 | 5/2005 | Jimenez et al. |
| 2005/0091769 A1 | 5/2005 | Jimenez et al. |
| 2005/0166344 A1 | 8/2005 | Hohlbein et al. |
| 2005/0172439 A1 | 8/2005 | Weihrauch |
| 2005/0188487 A1 | 9/2005 | Moskovich et al. |
| 2005/0188489 A1 | 9/2005 | Hohlbein |
| 2005/0210612 A1 | 9/2005 | Hohlbein et al. |
| 2005/0235439 A1 | 10/2005 | Braun et al. |
| 2005/0273961 A1 | 12/2005 | Moskovich |
| 2005/0278883 A1 | 12/2005 | Hohlbein |

(56) References Cited

U.S. PATENT DOCUMENTS

| | | |
|---|---|---|
| 2006/0026784 A1 | 2/2006 | Moskovich et al. |
| 2006/0052806 A1 | 3/2006 | Xi et al. |
| 2006/0057087 A1 | 3/2006 | Moskovich et al. |
| 2006/0075588 A1 | 4/2006 | Amador |
| 2006/0099162 A1 | 5/2006 | Moskovich et al. |
| 2006/0117508 A1 | 6/2006 | Hohlbein |
| 2006/0130257 A1 | 6/2006 | Cann |
| 2006/0168744 A1 | 8/2006 | Butler et al. |
| 2006/0195995 A1* | 9/2006 | Moskovich et al. ............ 15/111 |
| 2006/0200925 A1 | 9/2006 | Moskovich et al. |
| 2006/0272112 A9 | 12/2006 | Braun et al. |
| 2007/0006410 A1 | 1/2007 | Kramer |
| 2007/0067933 A1 | 3/2007 | Waguespack |
| 2007/0119736 A1 | 5/2007 | Kayser |
| 2007/0163064 A1 | 7/2007 | Wong et al. |
| 2007/0204417 A1 | 9/2007 | Russell et al. |
| 2007/0222426 A1 | 9/2007 | Waffenschmidt et al. |
| 2007/0226931 A1 | 10/2007 | Kayser |
| 2007/0251040 A1 | 11/2007 | Braun et al. |
| 2007/0271717 A1 | 11/2007 | Clos et al. |
| 2008/0050398 A1 | 2/2008 | Bockmuehl et al. |
| 2008/0060155 A1 | 3/2008 | Braun et al. |
| 2008/0141476 A1 | 6/2008 | Gatzemeyer et al. |
| 2008/0141478 A1 | 6/2008 | Gatzemeyer et al. |
| 2008/0184511 A1 | 8/2008 | Brown et al. |
| 2008/0196185 A1 | 8/2008 | Gatzemeyer et al. |
| 2008/0244849 A1 | 10/2008 | Moskovich et al. |
| 2008/0307596 A1 | 12/2008 | Hohlbein |
| 2008/0315668 A1 | 12/2008 | Huber et al. |
| 2009/0019649 A1 | 1/2009 | Dickie |
| 2009/0019650 A1 | 1/2009 | Dickie |
| 2009/0025165 A1 | 1/2009 | Moskovich et al. |
| 2009/0094768 A1 | 4/2009 | Hohlbein et al. |
| 2009/0172900 A1 | 7/2009 | Brown, Jr. et al. |

FOREIGN PATENT DOCUMENTS

| | | |
|---|---|---|
| EP | 1 011 376 B1 | 8/2007 |
| EP | 1834605 A1 | 9/2007 |
| EP | 1 653 828 B1 | 1/2008 |
| GB | 753862 | 8/1956 |
| JP | 07308222 A | 11/1995 |
| WO | WO 88/03772 A1 | 6/1988 |
| WO | WO 95/10959 A1 | 4/1995 |
| WO | WO9707707 | 3/1997 |
| WO | WO 98/00048 A1 | 1/1998 |
| WO | WO 98/05241 A1 | 2/1998 |
| WO | WO 98/27846 A1 | 7/1998 |
| WO | WO 98/34514 A1 | 8/1998 |
| WO | WO 99/37180 | 7/1999 |
| WO | WO 00/03619 A1 | 1/2000 |
| WO | WO 00/60980 A1 | 10/2000 |
| WO | WO 00/74522 A1 | 12/2000 |
| WO | WO 00/76370 A1 | 12/2000 |
| WO | WO 02/15740 A1 | 2/2002 |
| WO | WO 03/092435 A1 | 11/2003 |
| WO | WO 2006/012956 A2 | 2/2006 |
| WO | WO 2008/017996 A2 | 2/2008 |

* cited by examiner

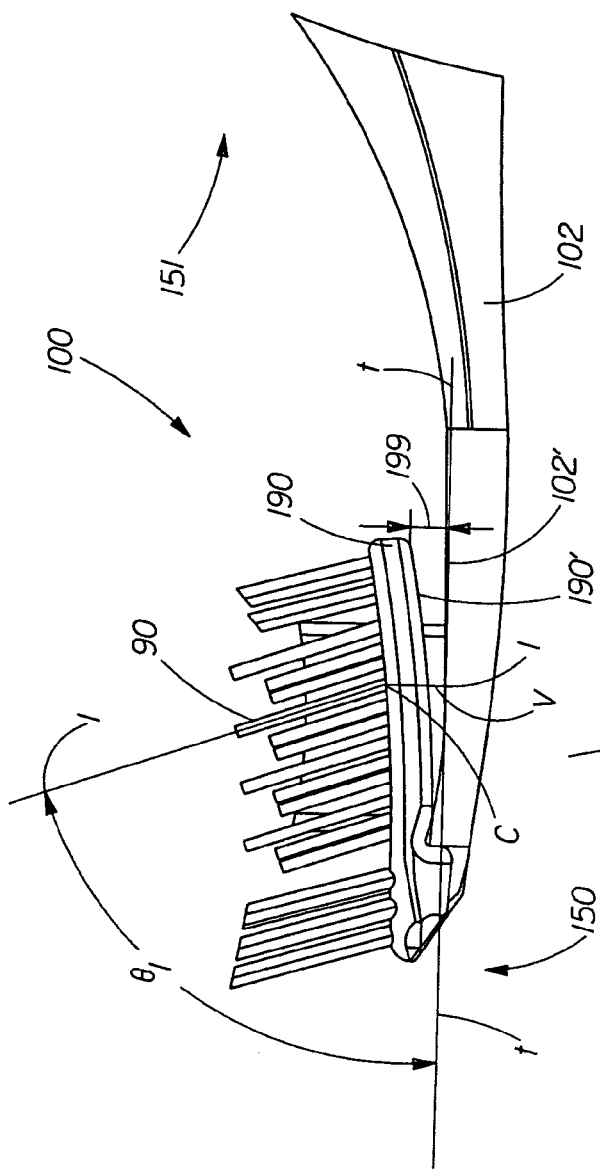

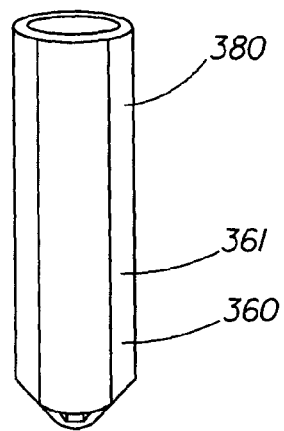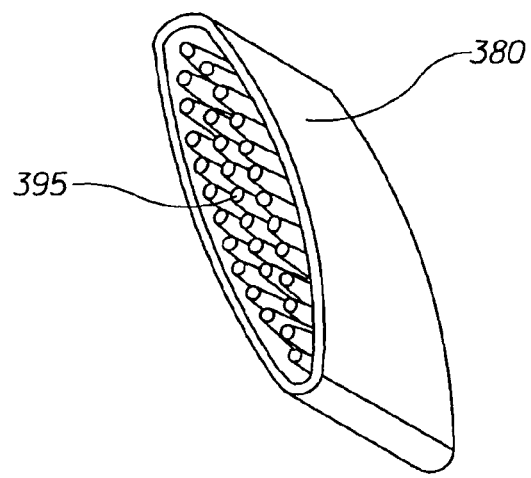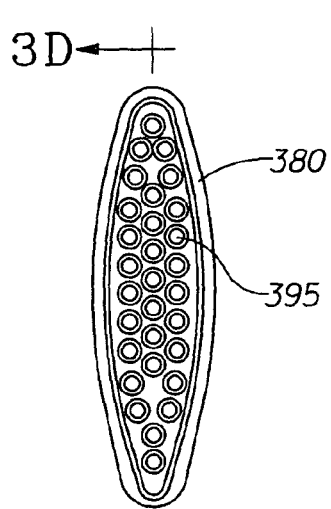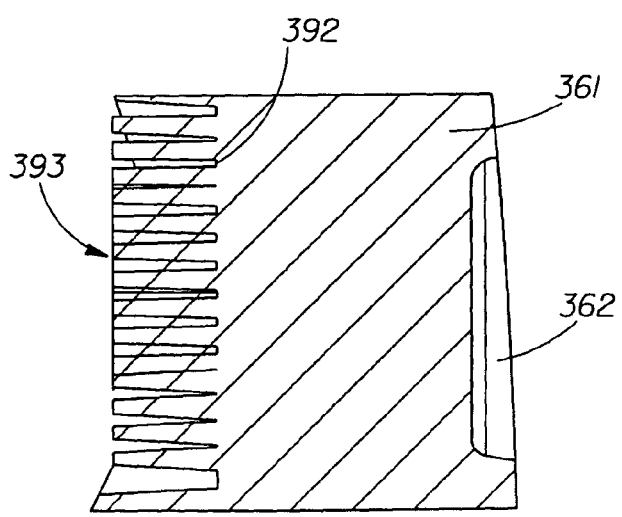
Fig. 3A
Fig. 3C
Fig. 3B
Fig. 3D

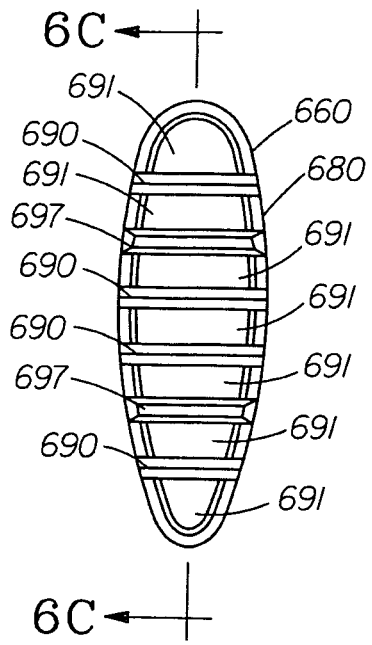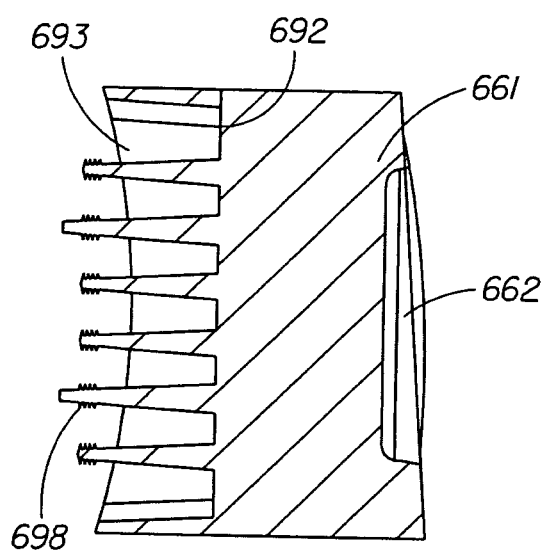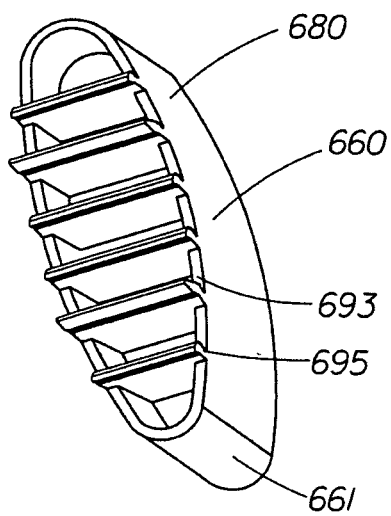
Fig. 6A
Fig. 6C
Fig. 6B

ORAL HYGIENE IMPLEMENTS HAVING FLEXIBLE ELEMENTS, AND METHODS OF MAKING THE SAME

CROSS REFERENCE

This application claims the benefit of U.S. Provisional Patent Application No. 60/899,051 filed on Feb. 2, 2007, entitled, "Oral Hygiene Implement Having a Flexible Head" and claims the benefit of U.S. Provisional Patent Application No. 60/928,711 filed on May 11, 2007, entitled, "Oral Hygiene Implement Having a Flexible Head", each application being incorporated herein by reference.

FIELD OF THE INVENTION

The present invention pertains to oral hygiene implements having flexible elements and to methods of making the same.

BACKGROUND OF THE INVENTION

The utilization of toothbrushes to clean one's teeth has long been known. A typical toothbrush includes a handle region, a neck region, and a head region. The neck region typically is disposed between and attaches the handle region to the head region.

Toothbrushes generally have a plurality of bristles disposed in the head region which extend outward from the head region. The head region generally includes a toe and a heel. The heel is generally joined to the neck region while the toe generally corresponds to an area of the head region which is proximate to a tip of the toothbrush. Typically, the user will utilize the toe of the toothbrush to reach the back teeth and for targeted cleaning.

In general, a user will typically apply a dentifrice to the bristles of the toothbrush and brush his/her teeth with the toothbrush and dentifrice combination. A user typically will apply a brushing force to the toothbrush to ensure that his/her teeth are adequately cleaned. This can be an arduous task due to the nature of the teeth. For example, the buccal or outer surfaces of the teeth may benefit more from a toothbrush with a concave bristle contour while the lingual and/or inner surfaces of the teeth may benefit more from a convex bristle contour. As such, the user may apply the brushing force in order to attempt to conform the head region to the oral surface to be cleaned.

However, because some conventional toothbrushes are relatively rigid, the brushing force required to conform the head region may cause damage to soft oral tissues and/or other oral surfaces. For example, in some conventional toothbrushes the bristles arranged toward the center of the head region can bear more of the brushing force than its other bristle counterparts. This localized brushing force can cause damage to the gums and wear the tooth enamel more than is necessary.

Consequently, a need exists for an oral hygiene implement which has a flexible head. Moreover, a need exists for an oral hygiene implement which reduces the brushing force which is born by the center of the head region of the oral implement.

SUMMARY OF THE INVENTION

Oral hygiene implements constructed in accordance with the present invention can provide an oral hygiene implement which has one or more flexible head elements. Additionally, oral hygiene implements constructed in accordance with the present invention can reduce the brushing force which is born by cleaning elements in the center of the head. Moreover, in some embodiments of the present invention, oral hygiene implements constructed in accordance with the present invention may reduce the brushing force which is born by the cleaning elements in the center of the head while still allowing full contact and use of the toe region of the oral hygiene implement.

In some embodiments, an oral hygiene implement includes a body having a distal end and a proximal end. The oral hygiene implement further comprises a carrier member and a bending area. The carrier member has a toe area and a heel area, wherein the toe area is attached to the body while the heel area is unattached to the body. The bending area is disposed between the toe area and the heel area thereby allowing the heel area to bend while the toe area stays fixed.

In some embodiments, an oral hygiene implement includes a body having a distal end and a proximal end. The oral hygiene implement further comprises a first carrier member and a second carrier member. The first carrier member has a first toe area and a first heel area, and the second carrier member has a second toe area and a second heel area. The first toe area and the second toe area are attached to the body while the first heel area and the second heel area are unattached to the body. Additionally, the first carrier member and the second carrier member are separated from one another in between the toe areas and the heel areas thereby creating an intermediate opening.

In some embodiments, an oral hygiene implement includes a handle region, a head region, and a neck region disposed between and attached to the handle region and the head region, a proximal end comprised by the head region and a distal end comprised by the handle region. The oral hygiene implement further comprises a first carrier member, and a second carrier member.

The first carrier member has a first toe area and a first heel area extending inboard from the first toe area. The first toe area is attached to the head region at the proximal end while the first heel area is unattached to the oral hygiene implement.

The second carrier member has a second toe area and a second heel area extending inboard from the second toe area. The second toe area is attached to the first toe area and attached to the head region at the proximal end while the second heel area is unattached to the oral hygiene implement. Additionally, the first carrier member and the second carrier member form an intermediate opening therebetween.

In some embodiments, an oral hygiene implement comprises a body having a distal end and a proximal end. The oral hygiene implement further comprises a first carrier member and a second carrier member extending inboard from the proximal end of the body. The first carrier member and the second carrier member are cantilevered from the proximal end of the body, and the first carrier member and the second carrier member form an opening therebetween.

In some embodiments, an oral hygiene implement may comprise a body having a first end and a second end. The oral hygiene implement may further comprise a head region comprising an inner region and an outer region, and a cleaning element carrier attached to the body and disposed in the head region. The inner region may be fixed and the outer region may be capable of moving with respect to the inner region. Also, herein the cleaning element carrier is disposed in the outer region.

Aspects and/or embodiments may have one or more of the following advantages. Some of the oral hygiene devices provide improved tracking across the complex topography of human teeth. Some oral hygiene devices have flexible center fields, which can enable the cleaning elements and/or massaging elements to surround and hug the teeth for enhanced cleaning and/or massaging action. Many oral hygiene devices have improved interproximal penetration and/or cleaning. The oral hygiene devices can work effectively within the user's established routine. The disclosed devices described can reduce gingival abrasion. Many the devices provide cleaning elements, such as polyamide bristles, which have an improved and variable angle of attack. Many of the devices provide power brush action in a manual format. Some of the devices work synergistically with a cleaning paste to improve the efficacy of the paste. For example, some of the devices can improve the whitening and/or polishing power of a cleaning paste. The devices can provide for motion in a direction of the teeth and gums while the user is using longitudinal motion perpendicular to that direction. The cleaning and/or massaging element carriers can be removed and replaced by another element that is the same or different than the removed element. The flexible head elements allow for the use of relatively large toe without impeding the cleaning and/or massaging action of other elements. An angle of one or more of the cleaning and/or massaging elements with respect to the body of the oral hygiene implement continuously changes during use, e.g., during brushing, which can increase the likelihood that all areas of the oral cavity are effectively cleaned and/or massaged. An amount of total possible implement area, e.g., brushing area, in contact with the oral cavity or a portion of the oral cavity can be adjusted during use of the implement. For example, an increase in the amount of the brush area in contact with the teeth can be achieved by the application of additional forces to the brush, giving the user control over the kind and amount of cleaning and/or massaging desired for a particular region of the oral cavity.

BRIEF DESCRIPTION OF THE DRAWINGS

FIGS. 1F and 1G are partial side views showing the toothbrush of FIG. 1A in its nominal state (FIG. 1F) and the toothbrush of FIG. 1A with a force applied to the element carrier (FIG. 1G).

FIGS. 3A-3D are an elevation view, a plan view, an isometric view, and a cross sectional view, each showing an intermediate member constructed in accordance with the present invention.

FIGS. 6A-6C are a plan view, an isometric view, and a cross sectional view, each showing another embodiment of an intermediate member constructed in accordance with the present invention.

DETAILED DESCRIPTION OF THE INVENTION

Definitions

"Cleaning element facing surface" and "Body facing surface" refer respectively to the relative location of an element, member, etc., or group of elements, members, etc. "Body facing surface" implies the surface is nearer to the body than some other surface of the element, member, etc. described. "Cleaning element facing surface" implies the surface is nearer to the cleaning elements than some other surface of the element, member, etc., described.

"Cleaning element carrier" as used herein refers to a structure upon which cleaning elements, massaging elements, and/or any suitable element for use in the oral cavity, etc., may be positioned.

The term "longitudinal" is used herein to refer to a direction which is generally parallel to the longest straight line distance between the two outermost points of a toothbrush. In the context of a toothbrush, a "longitudinal" axis may run from a point adjacent to or in a handle region up to and through a point adjacent or in the head region. Directions within ±30° of the longitudinal axis are considered to be "longitudinal".

The term "lateral" refers to a direction running generally perpendicular and in the same plane as the "longitudinal" direction, e.g. an xy plane. Directions within ±30° of a lateral direction are considered to be "lateral".

The term "transverse" refers to a direction running generally perpendicular to both the longitudinal and lateral directions. Additionally, the "transverse" direction lies in a plane which is perpendicular to the longitudinal and lateral directions, e.g. a yz plane. Directions within ±30° of a transverse direction are considered to be "transverse".

The "proximal end" of the cleaning element carrier refers to an end furthest away from the brush body. The "distal end" of the cleaning element carrier refers to an end of the carrier closest to the brush body.

Description

Figure 1A:
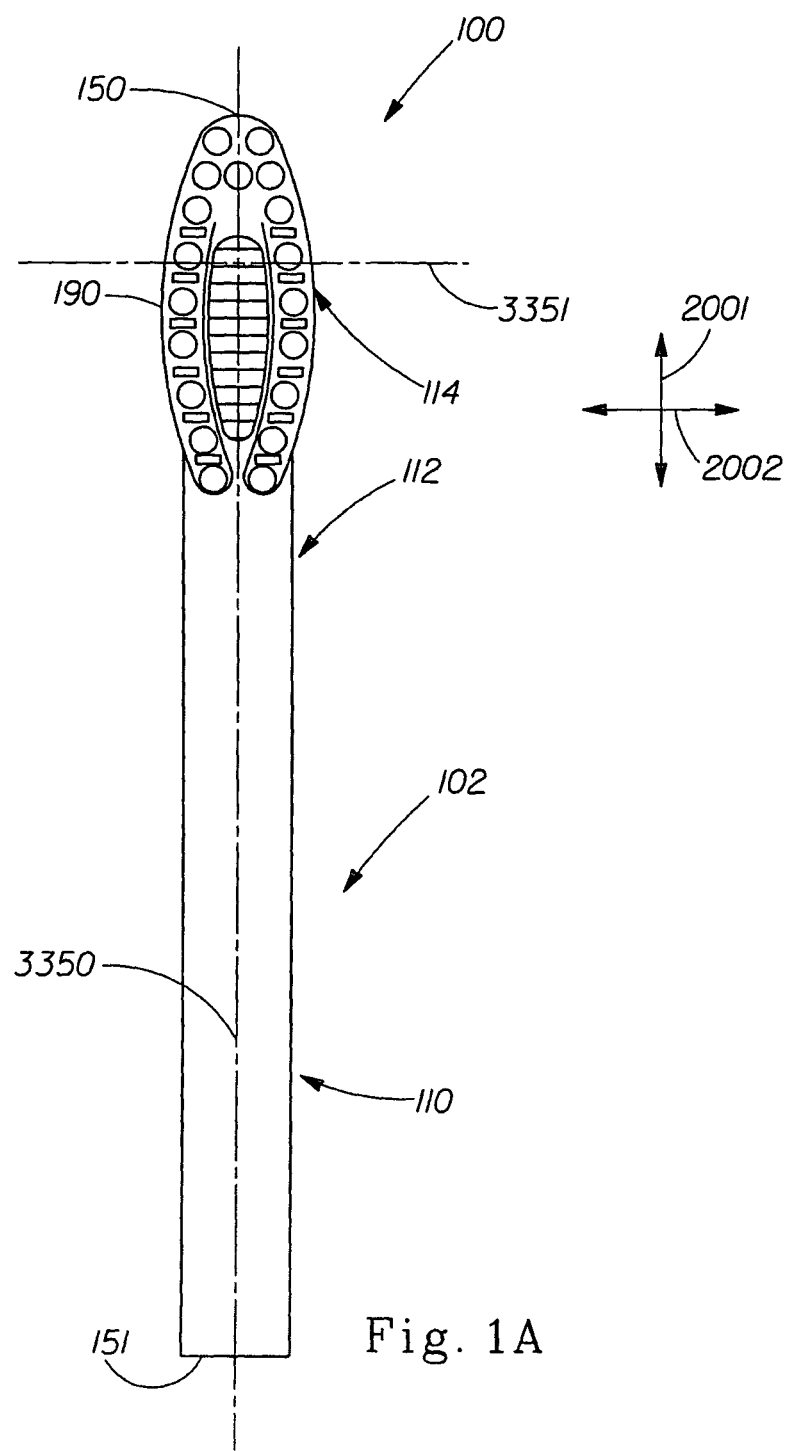
FIG. 1A is plan view showing a toothbrush constructed in accordance with the present invention.

As shown in FIG. 1A, an oral hygiene implement such as a toothbrush 100 constructed in accordance with the present invention may comprise a body 102. The body 102 may include a handle region 110, a neck region 112, and a head region 114. The neck region 112 can be disposed between and attached to the handle region 110 and the head region 114. The body 102 may further include a first end 150 and a second end 151. Additionally, the toothbrush 100 may further comprise a cleaning element carrier 190 which is attached to the body 102.

A longitudinal axis 3350 extends through the first end 150 and the second end 151. A lateral axis 3351 is generally perpendicular to the longitudinal axis 3350. A transverse axis (not shown) is generally perpendicular to the longitudinal axis 3350 and the lateral axis 3351 extending into and out of the sheet showing FIG. 1A.

Figure 1B:
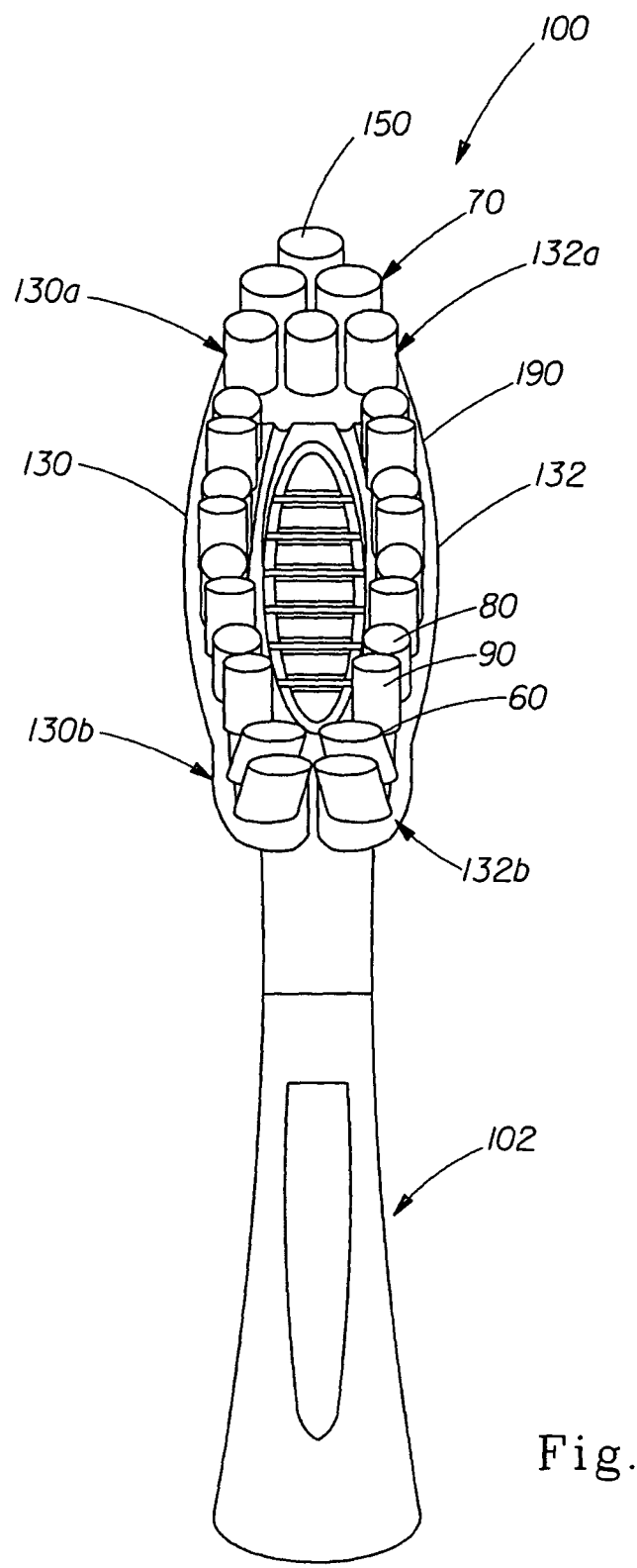
FIG. 1B is a partial plan view showing the toothbrush of FIG. 1A.

As shown in FIG. 1B, in some embodiments, the cleaning element carrier 190 may further comprise a first carrier member 130 and a second carrier member 132. As shown in FIG. 1B, the first and/or the second carrier members 130, 132 may support a variety of cleaning element fields, e.g. 60, 70, 80, and 90. Suitable cleaning elements for use in the present invention, such as bristles made of polyamide and or any other suitable material and/or various elastomeric elements, are discussed hereafter.

As shown the cleaning element carrier 190 may comprise a proximal area and a distal area. For example, the first carrier member 130 can have a first proximal area 130A and a first distal area 130B. Similarly, the second carrier member 132 may comprise a second proximal area 132A and a second distal area 132B. As shown, both the first distal area 130B and the second distal area 132B extend inboard from their respective proximal area.

In some embodiments, the first proximal area 130A may be attached to the second proximal area 132A. The first proximal area 130A may be attached to the second proximal area 132A by any suitable method. For example, the first proximal area 130A and the second proximal area 132A may be integrally formed together, e.g., by molding them as one piece. As another example, the first proximal area 130A and the second proximal area 132A may be attached adhesively. As yet another example, the first proximal area 130A and the second proximal area 132A may be welded together, e.g. ultrasonically. Other suitable examples for attaching, connecting, etc. the first proximal area 130A with the second proximal area 132A include snap fit, overmolding, interference fit, pins and corresponding pin openings, clips, thermal bonding, rivets, screws, solvent bonding, spin bonding and/or wraps, e.g., heat shrinkable wraps.

Additionally, embodiments are contemplated where the first proximal area 130A and/or the second proximal area 132A are integrally formed with the body 102, e.g., by forming them as the body is formed, e.g., by injection molding. Any suitable method may be utilized in integrally forming the first proximal area 130A and/or the second proximal area 132A with the body 102. Some suitable examples include machining, molding, casting, etc.

As shown in FIG. 1B, the first distal area 130B and the second distal area 132B may be separated from one another. However, embodiments are contemplated where the first distal area 130B and the second distal area 132B are attached to one another. Any suitable method may be utilized to attach the first distal area 130B and the second distal area 132B. Some suitable examples of such methods are provided above with regard to the attachment of the first proximal area 130A to the second proximal area 132A. For example, in some embodiments, the first distal area 130B and the second distal area 132B are attached by an elastomer, e.g., a polystyrene-based elastomer (e.g., styrene-ethylene-butylene-styrene block copolymer. In such embodiments, the movement of 130B and 132B are elastomerically coupled.

Figure 1C:
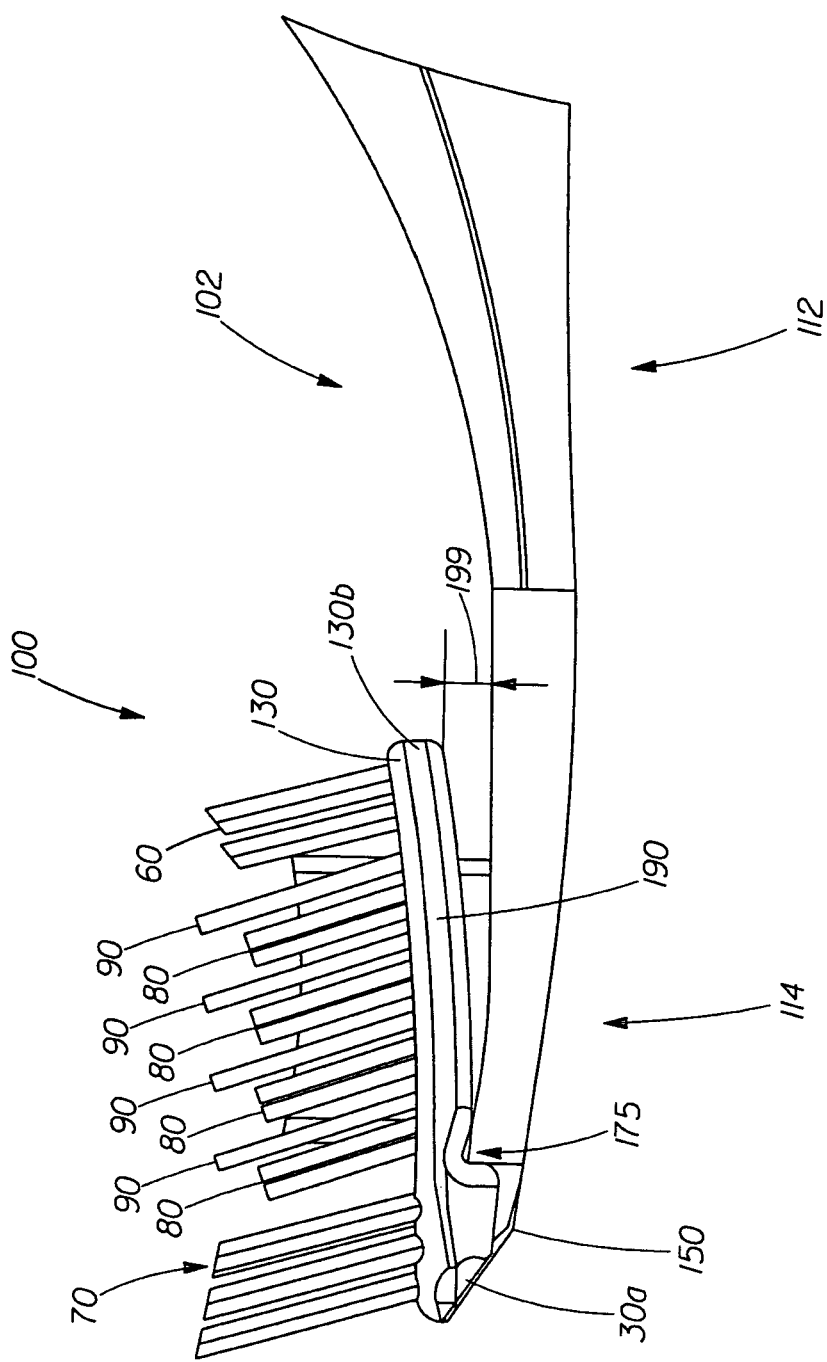
FIG. 1C is a partial side view showing the toothbrush of FIG. 1A.

As shown in FIG. 1C, in some embodiments, the cleaning element carrier 190 may be attached to the body 102 proximate to the first end 150 of the body 102. For example, the proximal area of the cleaning element carrier 190 may be attached to the body 102 proximate to the first end 150 and cantilevered or flexibly attached to the first end 150 of the body 102. As shown, the first proximal area 130A of the first carrier member 130 can be attached to the body 102 while the first distal area 130B extends inward from the first proximal area 130A and may be unattached to the body 102. The second carrier member 132 may be similarly configured, e.g. the second proximal area 132A may be attached to the body 102 while the second distal area 132B is unattached to the body.

Additionally, as shown, in some embodiments, the cleaning element carrier 190 may further comprise a bending element 175 disposed between the proximal area and the distal area of the cleaning element carrier 190. For example, as shown in FIG. 1C, the bending element 175 may be disposed between the first proximal area 130A and the first distal area 130B. The bending element 175 can separate the first proximal area 130A from the first distal area 130B.

The bending element 175 can ensure that the first distal area 130B is allowed to flex/bend/move in response to an applied brushing force while the first proximal area 130A stays fixed to the body 102. As such, the cleaning element field 70 can remain fixed while the cleaning element fields 60, 80, and 90 are allowed to flex/move with respect to the body 102. The bending element 175 can reduce the amount of bending/flexing that the first proximal area 130A and/or the cleaning element field 70 may experience in response to applied forces from brushing or other cleaning operations compared to the amount of bending/flexing of the remainder of the first carrier member 130. This reduction in bending/flexing of the first proximal area 130A and/or the cleaning element field 70 can increase the efficacy of the cleaning element field 70 over conventional oral hygiene implements. Additionally, oral hygiene implements constructed in accordance with the present invention may reduce the brushing force which is born by cleaning elements in the center of the cleaning element carrier, e.g. first carrier member 130 and/or second carrier member 132 as compared to conventional oral hygiene implements.

If desired, the entire distal end of the head below the cleaning elements can be encapsulated, e.g., by a membrane that serves to wall off and enclose the space defined between the top of the body and the bottom of the carrier. Such an embodiment can, e.g., provide the appearance of a solid structure for the consumer, and can prevent cleaning pastes and other debris from becoming lodged in the space. At the same time, such embodiments would still allow for the springing action of the element carrier.

Yet another benefit is that oral hygiene implements constructed in accordance with the present invention can provide improved tracking of cleaning elements along the tooth surface.

Figure 1D:
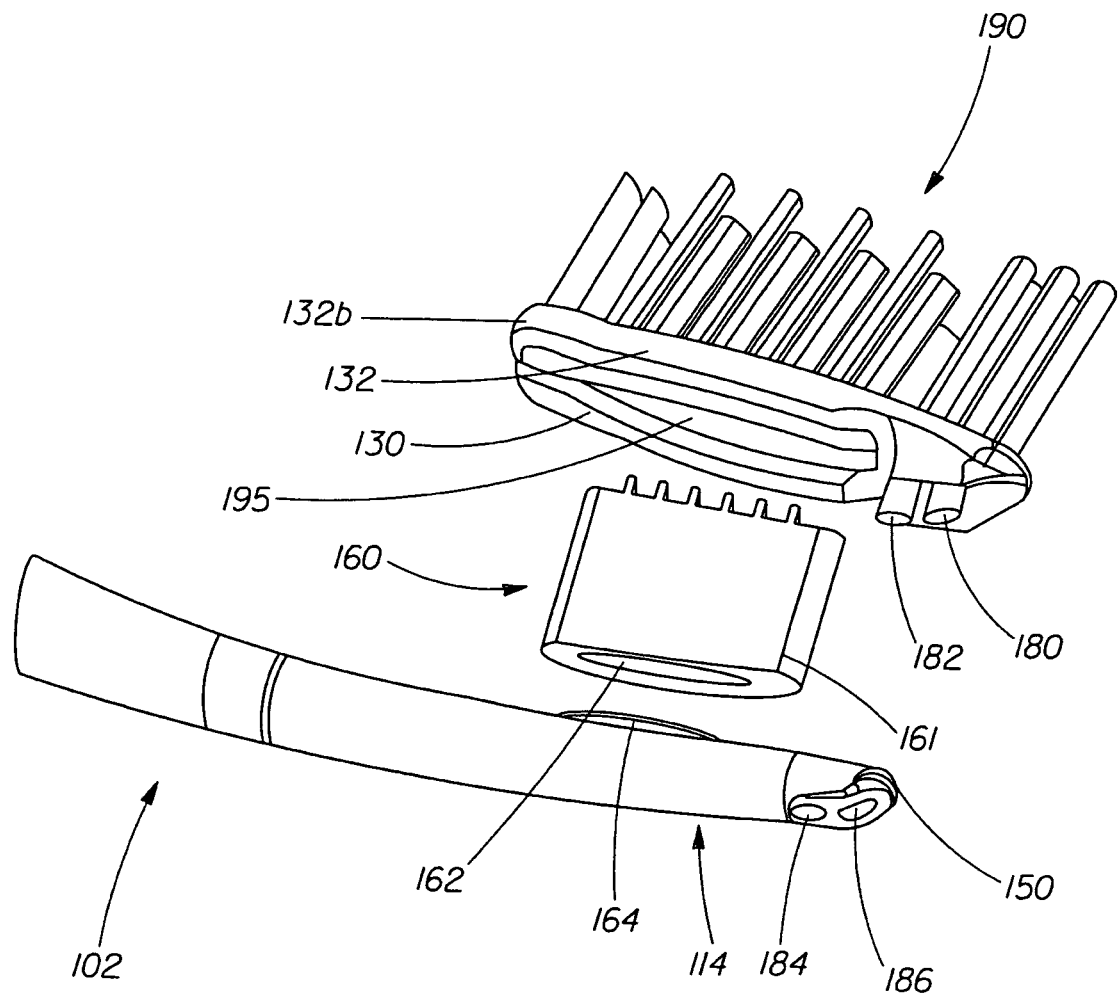
FIG. 1D is an exploded isometric view showing a bottom surface of the toothbrush of FIG. 1A.

For example, an intermediate member 160, as shown in FIG. 1D, for example, can provide a solid contact surface for cleaning of the broad flat surfaces of the teeth. Additionally, because the first proximal area 130A and/or the second proximal area 132A are fixed, they may provide sufficient reach around teeth situated more toward the front and provide contact to the teeth situated in the rear of the mouth. Also, the flexibility of the cleaning elements outside of the first proximal area 130A and/or the second proximal area 132A can allow the topography of the cleaning elements to move, flex, and maintain contact with the gumline and hard to reach interproximal regions.

The second carrier member 132 may be configured similarly to the first carrier member 130. For example, a separate bending element (not shown) may be included between the second proximal area 132A and the second distal area 132B thereby reducing the amount of bending/flexing that the second proximal area 132A experiences due to the pressure applied during brushing or other cleaning operations.

In some embodiments, the bending elements of the present invention may comprise weakened areas. For example, as shown in FIG. 1C, the bending element 175 may include an area having a reduced cross section of material as compared to a cross section of the first carrier member 130 and/or second carrier member 132 in the first distal area 130B and/or the second distal area 132B. In some embodiments, the cross section of the bending elements of the present invention may be between about 5% to about 99% of the cross section of the first carrier member 130 and/or second carrier member 132 in the first distal area 130B and/or the second distal area 132B, or any individual number within the range. In some embodiments, bending areas of the present invention may comprise a cross sectional area which is greater than about 5 percent of the cross sectional area of the first distal area 130B and/or second distal area 132B, greater than about 10 percent, greater than about 15 percent, greater than about 20 percent, greater than about 25 percent, greater than about 30 percent, greater than about 35 percent, greater than about 40 percent, greater than about 45 percent, greater than about 50 percent, greater than about 55 percent, greater than about 60 percent, greater than about 65 percent, greater than about 70 percent, greater than about 75 percent, greater than about 80 percent, greater than about 85 percent, and/or less than about 90 percent, less than about 85 percent, less than about 80 percent, less than about 75 percent, less than about 70 percent, less than about 65 percent, less than about 60 percent, less than about 55 percent, less than about 50 percent, less than about 45 percent, less than about 40 percent, less than about 35 percent, less than about 30 percent, less than about 25 percent, less than about 20 percent, less than about 15 percent, or less than about 10 percent of the cross sectional area of the first distal area 130B and/or the second distal area 132B.

In some embodiments, bending elements of the present invention may comprise a reduced cross sectional area from that of the proximal areas of the carrier member. In some embodiments, a carrier member may gradually decrease in cross sectional area from the proximal area to the distal area of the carrier member.

In some embodiments, the proximal area(s) and/or distal area(s) of the carrier member(s) may be constructed from a first material while the bending element comprises a second material which is different from the first material. For example, the bending element 175 may comprise a thermoplastic elastomer, such as a styrenic block copolymer, e.g., a styrene-ethylene-butylene-styrene block copolymer (SEBS), optionally, including an oil plasticizer, while the first carrier member 130 is constructed from a polypropylene, e.g., a high melt-flow index (MFI) polypropylene, such as a 10, 15, 20, 30, or 50 MFI polypropylene, or a styrene acrylonitrile material. In some embodiments, a bending element and a carrier are each made from the same basic material, but the bending element is softer than the carrier element. For example, the bending element can be formed of a thermoplastic elastomer, such as an SEBS polymer having a Shore A durometer of about 30, while the carrier can be formed from an SEBS polymer that is harder, e.g., 95 Shore A or 98 Shore A. The bending element which may be associated with the second carrier member 132 may be configured similarly. Additionally, in some embodiments, the distal area(s) may be constructed from a flexible material.

In embodiments where the bending element comprises a second material, as described above, the bending element may be integrally formed as part of the first carrier member 130 and/or the second carrier member 132. For example, the bending element can represent a "living hinge." Alternatively, the bending element may be discrete and attached to the first carrier member 130 and/or the second carrier member 132.

Additionally, as shown in FIG. 1C, the first carrier member 130 and/or the second carrier member 132 may be configured such that the first distal area 130B and/or the second distal area 132B are disposed superjacent to the body 102. Such a configuration may allow the first carrier member 130 and/or the second carrier member 132 a greater degree of flexibility when pressure is applied to the first carrier member 130 and/or the second carrier member 132. However, embodiments are contemplated where the first distal area 130B and/or the second distal area 132B are disposed in the same plane as the body 102. Additionally, embodiments are contemplated where the first distal area 130B and/or the second distal area 132B are disposed subjacent to the body 102.

In some embodiments, a distance 199 between an inwardmost point of the first distal area 130B and the body 102 and/or an inwardmost point of the second distal area 132B and the body 102 can be between about 0.01 mm and about 25 mm. In some embodiments, the distance 199 can be greater than about 0.01 mm, greater than about 1 mm, greater than about 2 mm, greater than about 3 mm, greater than about 4 mm, greater than about 5 mm, greater than about 6 mm, greater than about 7 mm, greater than about 8 mm, greater than about 9 mm, greater than about 10 mm, greater than about 11 mm, greater than about 12 mm, greater than about 13 mm, greater than about 14 mm, greater than about 15 mm, greater than about 16 mm, greater than about 17 mm, greater than about 18 mm, greater than about 19 mm, greater than about 20 mm, greater than about 21 mm, greater than about 22 mm, greater than about 23 mm, greater than about 24 mm, and/or less than about 25 mm, less than about 24 mm, less than about 23 mm, less than about 22 mm, less than about 21 mm, less than about 20 mm, less than about 19 mm, less than about 18 mm, less than about 17 mm, less than about 16 mm, less than about 15 mm, less than about 14 mm, less than about 13 mm, less than about 12 mm, less than about 11 mm, less than about 10 mm, less than about 9 mm, less than about 8 mm, less than about 7 mm, less than about 6 mm, less than about 5 mm, less than about 4 mm, less than about 3 mm, less than about 2 mm, or less than about 1 mm.

As shown in FIG. 1D, the cleaning element carrier 190 may be attached to the body 102 by any suitable means. For example, as shown, the cleaning element carrier 190 may comprise a first key 180 and/or a second key 182 which can be inserted into corresponding apertures. For example, the body 102 may comprise a first aperture 186 which is capable of receiving the first key 180 therein. Additionally, the body 102 may further comprise a second aperture 184 which is capable of receiving the second key 182 therein.

In some embodiments, the first key 180 and/or the second key 182 may be snap fitted into the first aperture 186 and/or the second aperture 184. In some embodiments, the first key 180 and/or the second key 182 may be adhesively attached to the first aperture 186 and/or the second aperture 184. In some embodiments, the first key 180 and/or the second key 182 may be welded to the surrounding material of the first aperture 186 and/or the second aperture 184. Any combination of the above methods may be utilized. Other suitable examples include overmolding, interference fit, clips, thermal bonding, rivets, screws, and/or wraps.

In some embodiments, the carrier element or a portion of the carrier element is configured to be removed by a consumer so that they can switch carriers (e.g., that are worn) with another similar or different element carrier. For example, one carrier can be used for cleaning and another element can be used for massaging the gums. In some embodiments, the keys work in conjunction with another implement so that the consumer can easily remove the carrier when desired, but otherwise the carrier remains fixed to the body.

Additionally, while the first key 180 and the second key 182 are illustrated in FIG. 1D, embodiments are contemplated where the cleaning element carrier 190 comprises only one key, e.g. the first key 180 or the second key 182. However, two keys may be beneficial to reduce the ability of the cleaning element carrier 190 to swivel with respect to the body 102.

In embodiments where the first proximal area 130A and the second proximal area 132A are unattached, the first carrier member 130 and the second carrier member 132 may each comprise a portion of the first key 180 and/or the second key 182. Alternatively, embodiments are contemplated where the first carrier member 130 comprise the first key 180 while the second carrier member 132 comprises the second key 182, or vice versa. In such embodiments, the first proximal area 130A and the second proximal area 132A may be attached or unattached as described heretofore.

Also, as shown in FIG. 1D, the first carrier member 130 and the second carrier member 132 may be separated from one another between the first proximal area 130A, the second proximal area 132A and the first distal area 130B and the second distal area 132B, thereby forming an intermediate opening 195. The intermediate member 160 may be attached to the body 102 such that the intermediate member 160 extends through the intermediate opening 195.

As shown, in some embodiments, the intermediate member 160 may comprise a unitary intermediate element 161. However, embodiments, are contemplated where the intermediate member 160 comprises a plurality of discrete elements.

The intermediate element 161 may be attached to the body 102 via any suitable means. For example, as shown, the intermediate element 161 may comprise an attachment cavity 162 adaptable for receiving an attachment key 164 on the body 102. Adhesive may be applied to the attachment key 164 and/or the attachment cavity 162 such that the intermediate element 161 is fixed to the body 102. As yet another example, the intermediate element 161 may be overmolded onto the body 102. Further embodiments of intermediate members and intermediate elements are provided with regard to FIGS. 2-17.

In some embodiments, the intermediate element 161 is configured to be removed by a consumer so that they can switch elements, such as those showing excessive wear, with another similar or different element. For example, one element can be used for cleaning, and another element can be used for enhanced whitening and/or polishing of the teeth. In some embodiments, the keys work in conjunction with another implement so that the consumer can easily remove the element when desired.

Figure 1E:
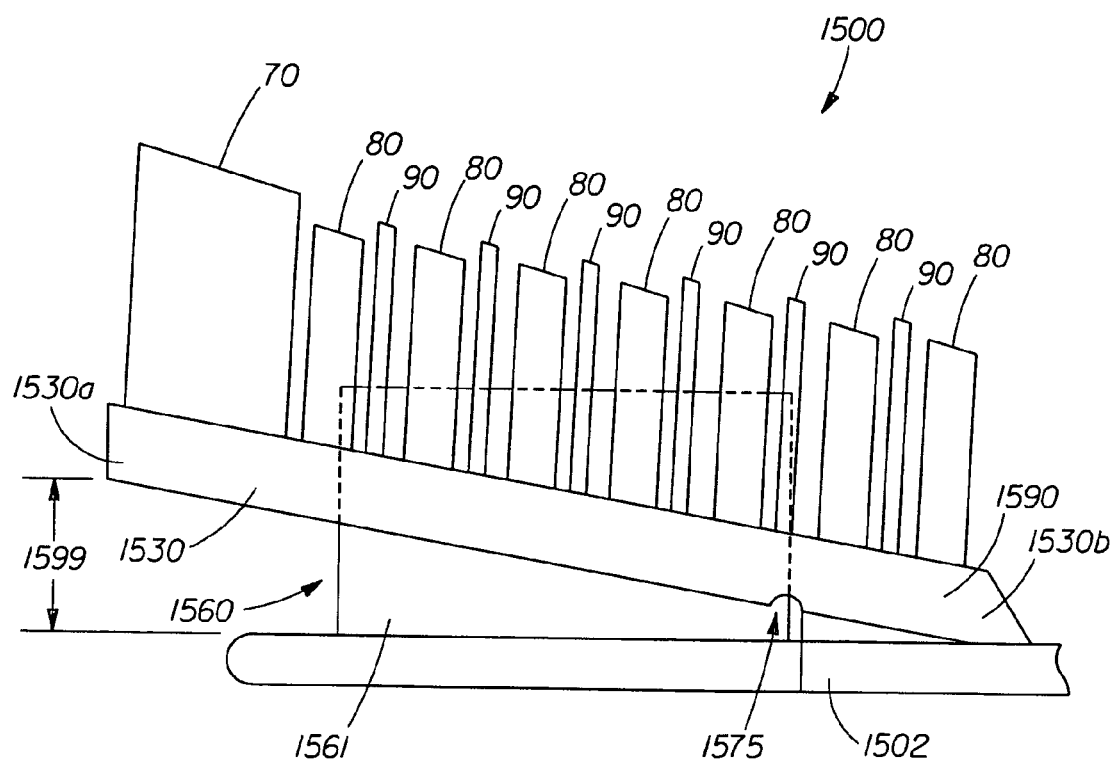
FIG. 1E is a partial side view showing an alternate embodiment of the toothbrush of FIG. 1A.

Referring back to FIG. 1C a cleaning element carrier 190 which is cantilevered from its proximal end, and thus has deflection properties for a given applied force that are a function of a distance from the proximal end, is shown; however, other embodiments are contemplated. For example, as shown in FIG. 1E, in some embodiments, a cleaning element carrier 1590 may be cantilevered from its distal area outward. As shown, a first carrier member 1530 having a first proximal area 1530A and a first distal area 1530B may be joined to a body 1502 such that the first distal area 1530B is attached to the body 1502 while the first proximal area 1530A is unattached to the body 1502.

Additionally, as shown, in some embodiments, the cleaning element carrier 1590 may further comprise a bending element 1575 disposed between the proximal area and the distal area of the cleaning element carrier 1590. For example, as shown in FIG. 1E, the bending element 1575 may be disposed between the first proximal area 1530A and the first distal area 1530B. The bending element 1575 can separate the first proximal area 1530A from the first distal area 1530B. Although not shown, a second carrier member may be configured similarly to the first carrier member 1530.

In contrast to the bending element 175 (shown in FIG. 1C), the bending element 1575 can ensure that the first proximal area 1530A is allowed to flex/bend in response to an applied brushing force while the first distal area 1530B stays fixed to the body 1502. As such, the cleaning element field 60, 80, and/or 90 can remain fixed while the cleaning element fields 60, 70, 80, and 90, which are disposed outside of the first distal area 1530B are allowed to flex. The bending element 1575 can reduce the amount of bending/flexing that the first distal area 1530B and/or the cleaning element fields 60, 80, and/or 90, may experience in response to applied forces from brushing or other cleaning operations compared to the amount of bending/flexing of the remainder of the first carrier member 1530. Oral hygiene implements constructed in accordance with the present invention may reduce the brushing force which is born by cleaning elements in the center of the head, e.g., first carrier member 130 and/or second carrier member 132, and the changing angle of attack with respect to a top surface of the body can improve cleaning in hard to reach locations, such as between the teeth.

Yet another benefit is that oral hygiene implements constructed in accordance with the present invention can provide improved tracking of cleaning elements along the tooth surface. For example, an intermediate member 1560 can provide a solid contact surface for cleaning of the broad flat surfaces of the teeth. Also, the flexibility of the cleaning elements outside of the first distal area 1530B and/or the second distal area can allow the topography of the cleaning elements to move, flex, and maintain contact with the gumline and hard to reach interproximal regions.

Additionally, oral hygiene implement constructed in accordance with the present invention may provide the benefit of having a fixed inner region and a movable/flexible outer region. For example, the cleaning element carrier may be allowed to bend or flex when brushing pressure is applied to the cleaning element carrier. However, because the intermediate member can be attached to the body, in some embodiments, the intermediate member can be fixed relative to the cleaning element carrier.

Although not shown, a second carrier member may be configured similarly to the first carrier member 1530. For example, a separate bending element (not shown) may be included between a second proximal area and the second distal area thereby reducing the amount of bending/flexing that the second distal area experiences due to the pressure applied during brushing or other cleaning operations.

The bending elements 1575 may be configured as described herein. With regard to FIG. 1E, embodiments are contemplated where the proximal area(s) comprise a flexible material.

Similar to the first carrier member 130 and the second carrier member 132 described herein, the first carrier member 1530 and the second carrier member may be attached to one another either at their respective distal areas and/or their respective proximal areas.

Additionally, similar to the cleaning element carrier 190 (shown in FIG. 1D), the first carrier member 1530 and the second carrier member may be separated from one another between the first proximal area 1530A, the second proximal area and the first distal area 1530B and the second distal area, thereby forming an intermediate opening. The intermediate member 1560 may be attached to the body 1502 such that the intermediate member 1560 extends through the intermediate opening.

In some embodiments, the first proximal area 1530A and/or the second proximal area may be disposed superjacent to the body 1502. Such a configuration may allow the first carrier member 1530 and/or the second carrier member a greater degree of flexibility when pressure is applied to the first carrier member 1530 and/or the second carrier member. However, embodiments are contemplated where the first proximal area 1530A and/or the second proximal area are disposed on the same plane as the body 1502. Additionally, embodiments are contemplated where the first proximal area 1530A and/or the second proximal area 1532A are disposed subjacent to the body 1502. A distance 1599 between an outwardmost point of the first proximal area 1530A and the body 102 and/or an outwardmost point of the second proximal area and the body 1502 can be as described heretofore with regard to the distance 1599.

The cleaning element carrier 1590 may be attached to the body 1502 by any suitable means. Some examples of suitable means are described herein with regard to the attachment of the cleaning element carrier 190 to the body 102. The body 1502 may be configured similarly to the body 102 described herein, and the cleaning element carrier 1590 may be configured similarly to the cleaning element carrier 190, except as noted herein.

In embodiments where the first distal area 1530B and the second distal area are unattached, the first carrier member 1530 and the second carrier member may each comprise a portion of a first key and/or a second key. Alternatively, embodiments, are contemplated where the first carrier member 1530 comprises the first key while the second carrier member comprises the second key, or vice versa. In such embodiments, the first distal area 1530B and the second distal area may be attached or unattached as described heretofore.

Although not shown, embodiments are contemplated where a first carrier member may be cantilevered from its proximal area while a second carrier member is cantilevered from its distal area. In such embodiments, the first carrier member and/or the second carrier member may be configured as described herein.

The intermediate member 1560 may be configured as described herein. For example, as shown in FIG. 1E, the intermediate member 1560 may comprise an intermediate element 1561. Additionally, the intermediate element 1561 may be attached to the body 1502 via any suitable means. Some examples of suitable means are described herein with regard to the attachment of the intermediate element 161 to the body 102. Other suitable configurations for the intermediate member 1560 and/or the intermediate element 1561 are discussed hereafter.

FIGS. 1F and 1G show that when a force (f) is applied directly (as shown) or indirectly (via the elements) to the carrier 190, an angle of one or more of the cleaning and/or massaging elements with respect to the body of the toothbrush changes as the spacing 199 between a top surface of the body 102' and a bottom surface of the carrier 190' changes, e.g., is reduced. During brushing of the teeth, typically the forces applied to the carrier are not static, but change during the brushing period. The changing of the spacing 199 changes the angle of one or more elements, e.g., bristle elements in the form of turfs or massaging elements in the form of elastomeric members. This changing angle with brushing can increase the likelihood that all areas of the oral cavity are effectively cleaned and/or massaged.

Referring particularly now to FIG. 1F for determining the above-discussed angle. As shown, the toothbrush 100 includes the body 102 that has the first end 150 and the second end 151. The cleaning and/or gum massaging element carrier 190 may extend from and over the body to define the spacing 199 between a lower surface of the carrier 190' and an upper surface of the body 102'. A first cleaning and/or gum massaging element 90 extends from the carrier at a first angle $\theta_1$ with respect to the body, when the carrier is in an undeflected position (its unloaded state). The first angle is measured in side view and is defined between a long axis (l) of the first cleaning and/or gum massaging element and a tangent line (t). The tangent line is defined by taking an imaginary vertical projection (v) extending vertically from a center (c) of the first cleaning and/or gum massaging element to intersect the upper surface of the body 102'. The vertical projection (v) is generally parallel to a transverse axis of the brush. The tangent line (t) is the imaginary line that is tangent to the upper surface 102' at the point of intersection (I).

Referring particularly now to FIG. 1G, upon application of a downward force (f) sufficient to reduce the spacing 199, the first cleaning element and/or massaging element defines a second angle $\theta_2$ different than the first angle when measured clockwise with respect to the tangent line. In some embodiments, for example those shown in FIG. 1E, the difference between the first angle and the second angle is measured counter-clockwise with respect to the tangent line.

As shown in FIGS. 1F and 1G, in some embodiments, the difference between the first angle and the second angle can vary among cleaning elements. For example, for those cleaning and/or massaging elements disposed adjacent to the connection between the cleaning and/or gum massaging element carrier 190 and the body 102, the difference between the first angle and the second angle may be less than the first angle and second angle difference for those cleaning and/or massaging elements disposed furthest away from the connection between the cleaning and/or gum massaging element carrier 190 and the body 102. In some embodiments, the second angle may be greater than the first angle. For example, the second angle may be greater than the first angle by greater than about 1 degree, 5 degrees, 10 degrees, 15 degrees, 20 degrees, 25 degrees, and/or less than about 25 degrees, 20 degrees, 15 degrees, 10 degrees, or less than about 5 degrees.

In the toothbrush exemplified in FIGS. 1F and 1G, the cleaning and/or gum massaging element carrier includes a plurality of cleaning and/or gum massaging elements extending from the carrier. In some embodiments, each cleaning and/or gum massaging element extends from the carrier, when the carrier is in the undeflected position, at the first angle with respect to the tangent line.

In some embodiments, the first angle may be between about 60 to about 135 degrees, e.g., between about 65 and about 120 degrees and/or the second angle may be between 75 degrees and about 135 degrees, e.g., between about 80 degrees and about 95 degrees. In some embodiments, the first angle and/or the second angle may be greater than about 60 degrees, 65 degrees, 70 degrees, 75 degrees, 80 degrees, 85 degrees, 90 degrees, 95 degrees, 100 degrees, 105 degrees, 110 degrees, 115 degrees, 120 degrees, 125 degrees, 130 degrees, 135 degrees, and/or less than about 140 degrees, 135 degrees, 130 degrees, 125 degrees, 120 degrees, 115 degrees, 110 degrees, 105 degrees, 100 degrees, 95 degrees, 90 degrees, 85 degrees, 80 degrees, 75 degrees, 70 degrees, or less than about 65 degrees.

Oral hygiene implements constructed comprising a first carrier member and a second carrier member which are not joined at their respective distal areas may allow the cleaning element carrier to have multiple movements. For example, referring back to FIG. 1, the first carrier member and/or the second carrier member may move/flex with in a direction generally parallel to the transverse axis of the brush. However, because the first carrier member and the second carrier member can move independently of one another, the first carrier member and the second carrier member may flex to the same extent or to varying extents, e.g. the first carrier member can flex to a greater extent than the second carrier member or vice versa. As another example, the first carrier member and/or the second carrier member may flex in a direction generally parallel to the lateral axis 3351. In some embodiments, the first carrier member and the second carrier member may move/flex along this direction to the same extent or to varying extents, e.g. the first carrier member may flex inward/outward to a greater extent than does the second carrier member or vice versa. Additionally, it is contemplated that the first carrier member and/or the second carrier member may move/flex while the other carrier member moves/flexes.

The flexibility of the first carrier member and/or the second carrier member can allow the bristle field of the toothbrush to conform more easily to the contour of a tooth. This easier conformance may increase the contact area of the bristle field and may increase the efficacy of the bristle field.

Figure 2:
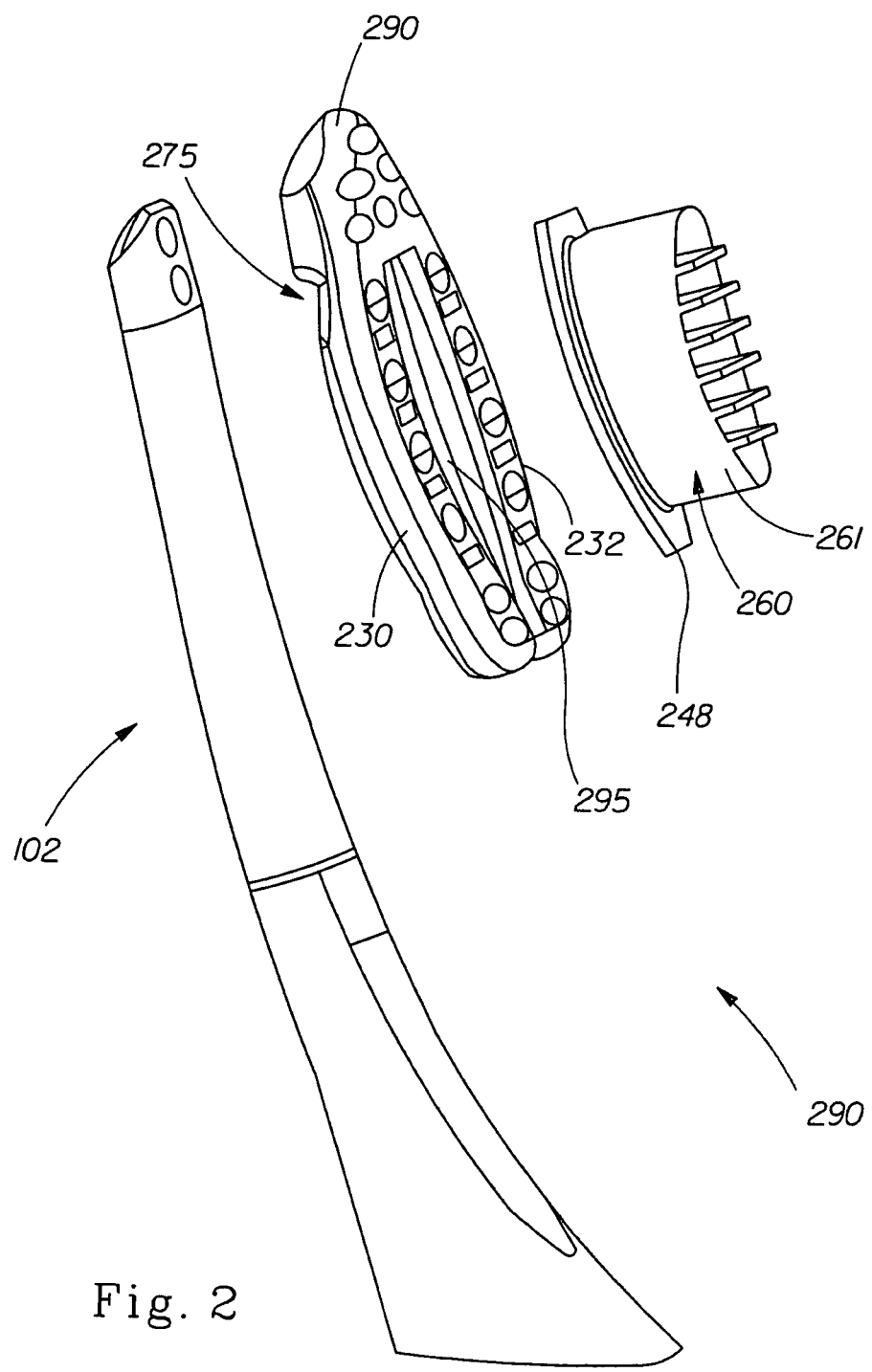
FIG. 2 is an exploded isometric view showing a portion of a toothbrush, the toothbrush being constructed in accordance with the present invention.

Referring now to FIG. 2, a portion of a toothbrush 200 is illustrated in accordance with an alternative embodiment, whereby reference numerals of elements illustrated in FIG. 2 corresponding to like elements, members, etc. of FIGS. 1A-1D are incremented by 100 for the purposes of clarity and convenience. A cleaning element carrier 290 is shown without the associated cleaning elements in order to facilitate the visual perception of some of the discussed features. In some embodiments, a first carrier member 230 and a second carrier member 232 may form an intermediate opening 295 therebetween. An intermediate member 260 may comprise a suspension layer 248 and an intermediate element 261. The suspension layer 248 may extend between the first carrier member 230 and the second carrier member 232 such that the suspension layer 248 is disposed in the intermediate opening 295. Alternatively, the suspension layer 248 may be attached to the first carrier member 230 and/or the second carrier member 232 on a cleaning element facing surface or a body facing surface of the carrier members. An intermediate member 260 may be attached to the suspension layer 248 and extend outward therefrom.

The suspension layer 248 may be attached to the first carrier member 230 and/or the second carrier member 232 by any suitable means. For example, the suspension layer 248 may be adhesively joined to the first carrier member 230 and/or the second carrier member 232. As yet another example, the suspension layer 248 may be overmolded onto the first carrier member 230 and/or the second carrier member 232.

Additionally, embodiments are contemplated where a rigid member(s) is joined to the suspension layer 248. In these embodiments, the rigid member can be joined to the first carrier member 230 and/or the second carrier member 232 by any suitable means. Some examples of suitable methods for attaching the rigid member are described herein.

Additionally, the suspension layer 248 may be joined to the intermediate element 261 by any suitable means. For example, the suspension layer 248 may be adhesively joined to the intermediate element 261. As yet another example, the suspension layer 248 may be integrally formed with the intermediate element 261, e.g. overmolded together.

Additionally, as shown, in some embodiments, the cleaning element carrier 290 may further comprise a first bending element 275 associated with the first carrier member 230 and/or a second bending element (not shown) associated with the second carrier member 232. The first bending element 275 and the second bending element may be configured as described heretofore with regard to the bending elements of the present invention.

Referring now to FIGS. 3A-3D, an intermediate member in accordance with an alternative embodiment of the present invention may be of any suitable configuration depending on the type of benefit(s) sought. For example, as shown in FIG. 3A, where massaging and/or dentifrice retention is sought, an intermediate member 360 may comprise an intermediate element 361 having an outer wall 380 forming a cavity therein thereby allowing the intermediate element 361 to retain a dentifrice or teeth cleaning composition.

Additionally, the intermediate element 361 may further comprise a plurality of projections 395 extending outward from an intermediate surface 392. At least some of the projections may taper from the intermediate surface 392 to an outer wall surface 393 or vice versa, in some embodiments. Embodiments are contemplated where at least some of the projections maintain a substantially constant cross sectional area (within 20%) from the intermediate surface 392 to the outer wall surface 393.

As shown in FIG. 3D, in some embodiments, at least some of the plurality of projections 395 may terminate at the outer wall surface 393 of the intermediate member 360. However, embodiments are contemplated where at least some of the plurality of projections 395 extend and terminate beyond the outer wall surface 393. The outer wall surface 393 can be flat, can be convex, can be concave, or a combination thereof.

Additionally, the intermediate element 361 may comprise an attachment cavity 362 adaptable for receiving a corresponding attachment key on the body, similar to the intermediate element 161. However, the intermediate element 361 may similarly be configured to be disposed on a suspension layer as discussed previously with regard to the intermediate element 261 (shown in FIG. 2).

Referring now to FIGS. 4A-4D, an intermediate member 460 constructed in accordance with the present invention is depicted. Similar to the intermediate member 360, the intermediate member 460 may comprise an intermediate element 461 having an outer wall 480. Additionally, the intermediate element 461 may further comprise a plurality of flaps 490. As depicted, the flaps 490 may extend from one portion of the outer wall 480 to another portion of the outer wall 480 thereby creating a plurality of receptacles 491.

The flaps 490 may be attached and/or integrally formed with the outer wall 480 and an intermediate surface 492, in some embodiments, thereby allowing at least some of the receptacles 491 to be isolated from adjacent receptacles. Alternatively, in some embodiments, at least some of the flaps 490 may be unattached to the intermediate surface 492 and/or unattached to the outer wall 480.

Figure 4A:
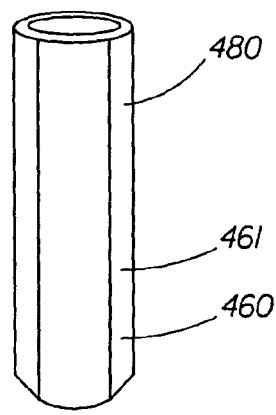
FIGS. 4A-4D are an elevation view, a plan view, an isometric view, and a cross sectional view, each showing another embodiment of an intermediate member constructed in accordance with the present invention.
Figure 4C:
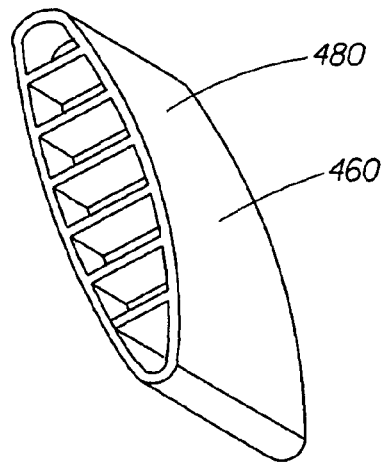
Figure 4B:
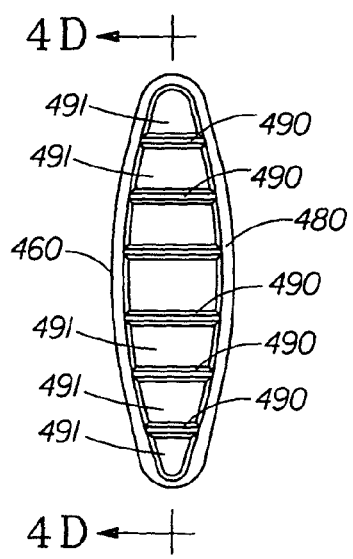
Figure 4D:
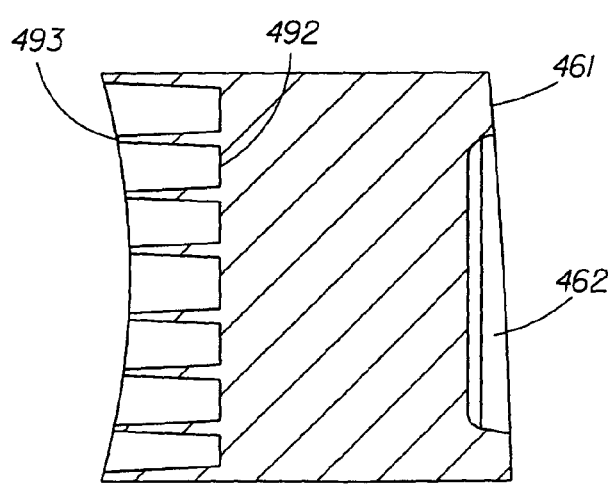

As shown in FIG. 4D, each of the plurality of flaps 490 may extend outward from the intermediate surface 492 and terminate at an outer wall surface 493 of the intermediate element 461. However, embodiments are contemplated where at least some of the flaps 490 extend and terminate beyond the outer wall surface 493. At least some of the flaps 490 may taper from the intermediate surface 492 to the outer wall surface 493 or vice versa, in some embodiments. Embodiments are contemplated where at least some of the flaps 490 maintain a substantially constant cross sectional area (within 20%) from the intermediate surface 492 to the outer wall surface 493.

Additionally, the intermediate element 461 may comprise an attachment cavity 462 adaptable for receiving a corresponding attachment key on the body, similar to the intermediate element 161. However, the intermediate element 461 can similarly be configured to be disposed on a suspension layer as discussed previously with regard to the intermediate element 261 (shown in FIG. 2).

Figure 5A:
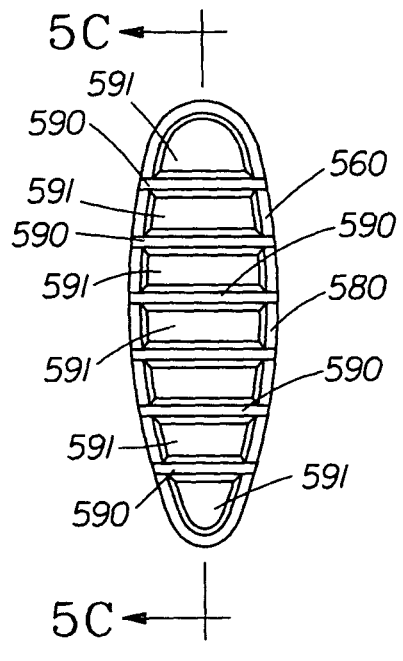
FIGS. 5A-5C are a plan view, an isometric view, and a cross sectional view, each showing another embodiment of an intermediate member constructed in accordance with the present invention.
Figure 5C:
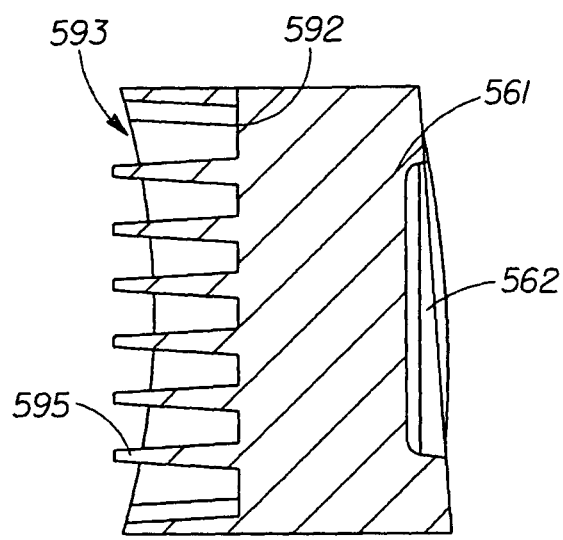
Figure 5B:
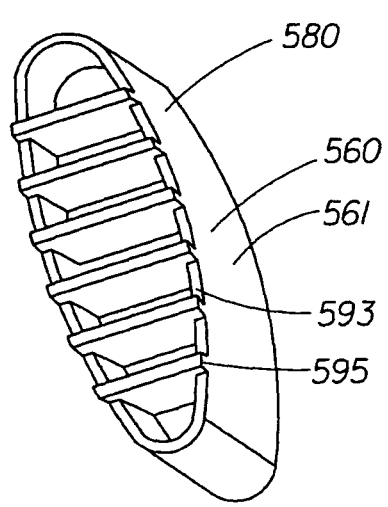

Referring now to FIGS. 5A-5C, an intermediate member 560 constructed in accordance with the present invention is depicted. Similar to the intermediate members 460, the intermediate member 560 may comprise an intermediate element 561 having an outer wall 580 and a plurality of flaps 590. The flaps 590 may be configured as discussed previously with regard to the flaps 490, thereby creating a plurality of receptacles 591.

As shown in FIG. 5C, each of the plurality of flaps 590 may extend outward from an intermediate surface 592. At least some of the flaps 590 may taper from the intermediate surface 592 to an end 595 or vice versa, in some embodiments. Embodiments are contemplated where at least some of the flaps 590 maintain a substantially constant cross sectional area (within 20%) from the intermediate surface 592 to the end 595.

As shown, the flaps 590 may extend and terminate beyond an outer wall surface 593. Additionally, the flaps 590 may form a portion of the outer wall surface 593 such that the outer wall surface 593 is non-uniform. For example, as shown in FIG. 5B, the ends 595 may form crests in the outer wall surface 593. Depending upon the shape of the ends 595, the outer wall surface 593 may be given any suitable design. For example, where the ends 595 are substantially square, the outer wall surface 593 may appear castellated. Other end shapes are contemplated such that the outer wall surface 593 appears wavy, serrated, saw blade like, etc. Any suitable shape may be utilized.

Additionally, the intermediate element 561 may comprise an attachment cavity 562 adaptable for receiving a corresponding attachment key on the body, similar to the intermediate element 161. However, the intermediate element 561 can similarly be configured to be disposed on a suspension layer as discussed previously with regard to the intermediate element 261 (shown in FIG. 2).

Figure 5D:
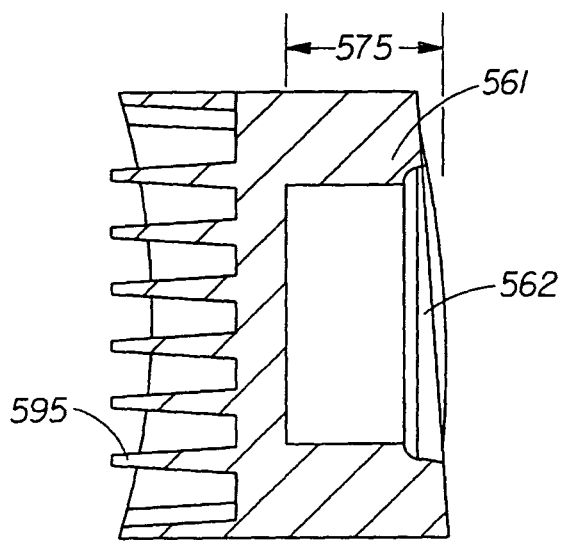
FIG. 5D is a cross sectional view showing another embodiment of the intermediate member of FIGS. 5A-5C.

As shown in FIG. 5D, the attachment cavity 562 may have a depth 575 which is a substantial portion of the overall depth of the intermediate element 561. For example, the depth 575 may be between about 10% to about 90% of the depth of the intermediate element 561, or any individual number within the range. In some embodiments, the depth 575 may be greater than about 10%, greater than about 20%, greater than about 30%, greater than about 40%, greater than about 50%, greater than about 60%, greater than about 70%, greater than about 80%, and/or less than about 90%, less than about 80%, less than about 70%, less than about 60%, less than about 50%, less than about 40%, less than about 30%, less than about 20%, or less than about 10%.

The increased depth 575 of the attachment cavity 562 may help stabilize the intermediate element 561 on the body of a toothbrush. For example, where the depth 575 of the attachment cavity 562 is increased and the length of the corresponding attachment key is increased, the intermediate element 561 can be further stabilized on the body.

Alternatively, where the depth 575 of the attachment cavity 562 is increased and the length of the corresponding attachment key is less than about 90% of the depth 575 of the attachment cavity 562, an air gap in the intermediate member 560 can be created. The air gap can provide additional flexibility and/or freedom of motion to the intermediate member 560. In some embodiments, the length of the corresponding attachment key can be less than about 90% and greater than about 2% of the depth 575 of the attachment cavity, or any individual number within the range. In some embodiments, the length of the corresponding attachment key can be less than about 90%, less than about 80%, less than about 70%, less than about 60%, less than about 50%, less than about 40%, less than about 30%, less than about 20%, less than about 10%, less than about 5%, and/or greater than about 2%, greater than about 5%, greater than about 10%, greater than about 20%, greater than about 30%, greater than about 40%, greater than about 50%, greater than about 60%, greater than about 70%, greater than about 80%, or greater than about 85%.

Any of the attachment cavities and/or attachment keys discussed heretofore and/or hereafter may be configured as described with regard to the intermediate element 561.

Referring now to FIGS. 6A-6C, an intermediate member 660 constructed in accordance with the present invention is depicted. Similar to the intermediate members 460 and 560, the intermediate member 660 may comprise an intermediate element 661 having an outer wall 680 and a plurality of flaps 690 and 697. The flaps 690 and/or 697 may be configured as discussed previously with regard to the flaps 490, thereby creating a plurality of receptacles 691, which can entrap cleaning pastes and enhance cleaning and/or whitening.

As shown in FIG. 6C, each of the plurality of flaps 690 and/or 697 may extend outward from an intermediate surface 692. The flaps 690 and/or 697 may form a portion of the outer wall surface 693 such that the outer wall surface 693 is non-uniform. The outer wall surface 693 may be configured as described above with regard to the outer wall surface 593.

As shown, the extent to which the flaps 690 and 697 extend from the intermediate surface 692 may vary. For example, in some embodiments, the flaps 690 may extend from the intermediate surface 692 to a lesser extent than the flaps 697 or vice versa. Additionally, the flaps 697 may be adjacent one another while the flaps 690 are distributed throughout the rest of the intermediate member 660. Alternatively, the flaps 697 may be spaced from one another by one or more flaps 690. Any suitable configuration of the flaps 690 and 697 may be utilized. The spacing of the flaps 697 may facilitate the interdental penetration of the flaps 697. For example, the spacing between flaps can be equal to an average spacing between all teeth or a portion of a set of teeth. For example, the spacing between flaps can be, e.g., between about 2.5 mm and about 15 mm, between about 5 mm and about 13 mm or between about 6 mm and about 11 mm. If desired, the flaps may be angled with respect to a longitudinal axis of the body at angles other than 90 degrees. For example, the flaps may be angled with respect to the longitudinal axis of the brush (measured clockwise) from about 55 degrees to about 88 degrees, e.g., from about 60 degrees to about 85 degrees or from about 65 degrees to about 82 degrees.

Each of the flaps 690 and 697 comprises an end region 695. As shown, at least one of the flaps 690 and/or 697 comprises ridges 698 disposed in the end region 695 of the flaps 690 and/or 697. The ridges 698 can increase efficacy of the cleaning of the flaps 690 and/or 697. Additionally, the ridges 698 may be integrally formed with the flaps 690 and/or 697. Alternatively, the ridges 698 may be discrete part attached to the flaps 690 and/or 697. In some embodiments, the ridges 698 may be formed from a material which is different from a material utilized for the flaps 690 and/or 697. In some embodiments, the ridges 698 may be formed from the same material as the flaps 690 and/or 697, e.g. thermoplastic elastomers, such as SEBS (styrene-ethylene-butylene-styrene block copolymer) or thermoplastic polyurethane (TPU). In some embodiments, the ridges 698 may be softer than the flaps 690 and/or 697. Alternatively, in some embodiments, at least some of the ridges 698 may be harder than the flaps 690 and/or 697. Suitable materials, processes, and design for the ridges 698 and the flaps are further described in U.S. Patent Application Publication No. 2005/0235439. Additionally, any of the flaps, protrusions, outer walls, etc. discussed herein may include ridges.

As shown in FIG. 6C, the intermediate element 661 may comprise an attachment cavity 662 adaptable for receiving a corresponding attachment key on the body, similar to the intermediate element 161. However, the intermediate element 661 can similarly be configured to be disposed on a suspension layer as discussed previously with regard to the intermediate element 261 (shown in FIG. 2).

Figure 7A:
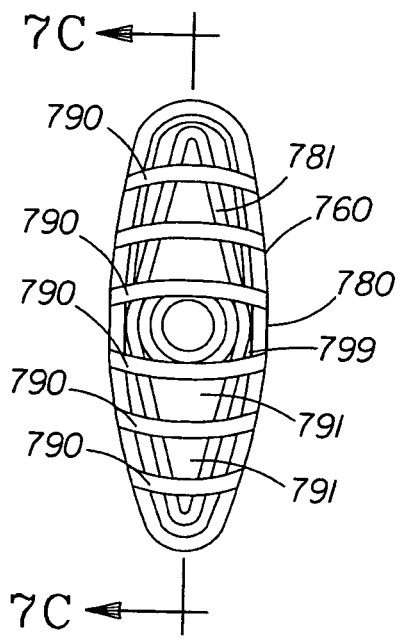
FIGS. 7A-7C are a plan view, an isometric view, and a cross sectional view, each showing another embodiment of an intermediate member constructed in accordance with the present invention.
Figure 7C:
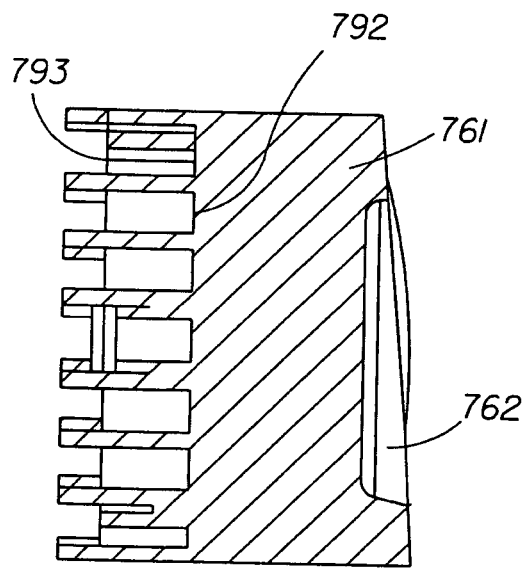
Figure 7B:
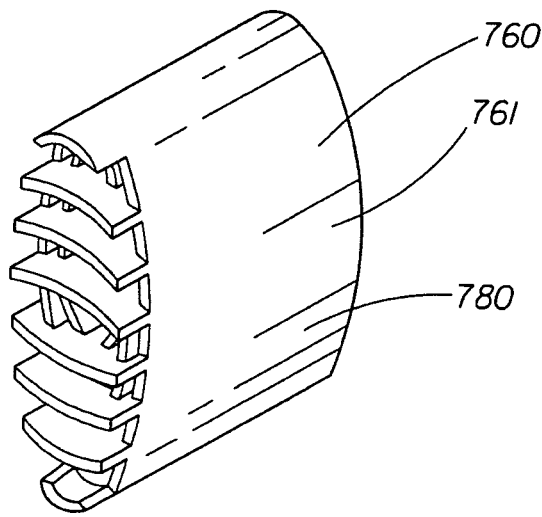

Referring now to FIGS. 7A-7C, an intermediate member 760 constructed in accordance with the present invention is depicted. Similar to the intermediate members 460, 560, and 660, the intermediate member 760 may comprise an intermediate element 761 having an outer wall 780 and a plurality of flaps 790. The flaps 790 may be configured as discussed previously with regard to the flaps 490, thereby creating a plurality of receptacles 791.

Additionally, as shown, the intermediate element 761 may further comprise an inner wall 781 and a cup 799. The inner wall 781 can be disposed within the outer wall 780. The inner wall 781 may be continuous or discontinuous. The cup 799 may be formed within the inner wall 781 of the intermediate member 760.

As shown, at least some of the plurality of flaps 790 may be curvilinear. For example, as shown, the flaps 790 may be concave with respect to the cup 799. As another example, the flaps 790 may be convex with respect to the cup 799. As yet another example, at least some of the flaps 790 may be convex with respect to the cup 799 while some of the flaps 790 are concave with respect to the cup 799. In still another example, some of the flaps 790 may comprise a complex curvature and comprise both convex and concave portions with respect to the cup 799. The curvilinear flaps may provide added structure and rigidity, thereby maintaining contact with the curved tooth surfaces.

As shown in FIG. 7C, each of the plurality of flaps 790 may extend outward from an intermediate surface 792. The flaps 790 may form a portion of the outer wall surface 793 such that the outer wall surface 793 is non-uniform as described previously with regard to the outer wall surface 593 (shown in FIG. 5C). The flaps 790 may be configured as described heretofore with regard to the flaps 590, 690, and/or 697.

Additionally, the intermediate element 761 may comprise an attachment cavity 762 adaptable for receiving a corresponding attachment key on the body, similar to the intermediate member 160. However, the intermediate element 761 can similarly be configured to be disposed on a suspension layer as discussed previously with regard to the intermediate element 261 (shown in FIG. 2).

Figure 8A:
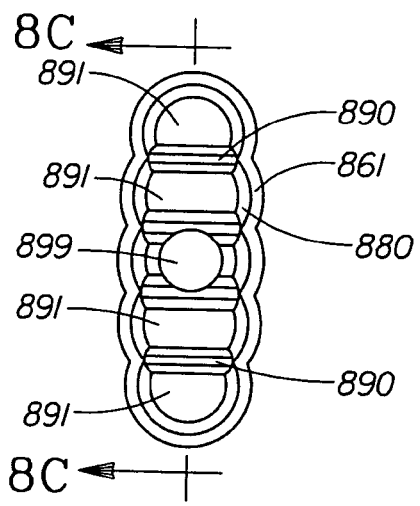
FIGS. 8A-8C are a plan view, an isometric view, and a cross sectional view, each showing another embodiment of an intermediate member constructed in accordance with the present invention.
Figure 8C:
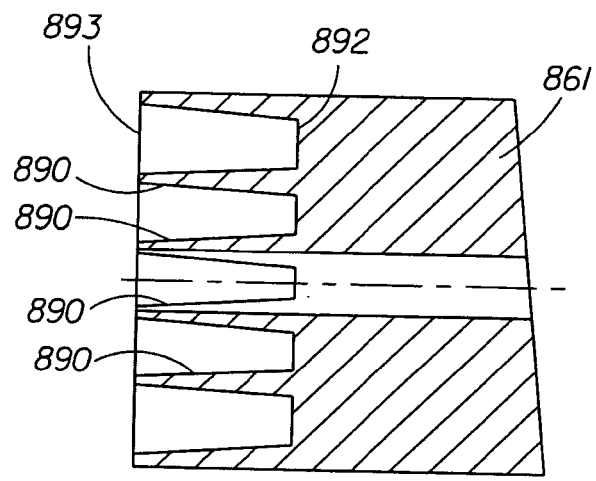
Figure 8B:
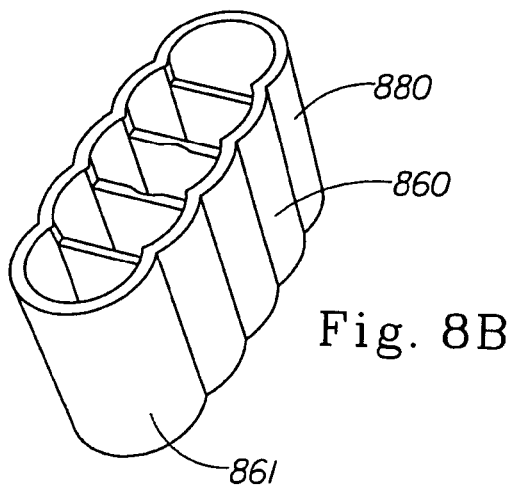

Referring now to FIGS. 8A-8C, an intermediate member 860 constructed in accordance with the present invention is depicted. Similar to the intermediate members 460, 560, 660, and 760, the intermediate member 860 may comprise an intermediate element 861 having an outer wall 880 and a plurality of flaps 890. However, as shown, in some embodiments, the outer wall 880 may be provided with some contour, e.g. arcuate portions, which give the intermediate element 861 a corrugated appearance. The outer walls 380, 480, 580, 680, and 780, as well as those discussed hereafter may be contoured similarly or in any suitable fashion. The flaps 890 may be configured as discussed previously with regard to the flaps 490, thereby creating a plurality of receptacles 891.

Additionally, as shown, the intermediate element 861 may further comprise an aperture 899. The aperture 899 may be configured to receive an electronic device, for example a light. As another example, the aperture 899 may be configured such that a dentifrice or other suitable chemistry may be dispensed therethrough. The intermediate member 860 may comprise any suitable number of apertures, e.g. one, two, three, four, five, six, seven, or more, etc.

The flaps 890 may extend from an intermediate surface 892. As shown, the flaps 890 may terminate in between an intermediate surface 892 and the outer wall surface 893. Alternatively, the flaps 890 may form a portion of the outer wall surface 893 such that the outer wall surface 893 is non-uniform as described previously with regard to the outer wall surface 593 (shown in FIG. 5C). The flaps 890 may be configured as described heretofore with regard to the flaps 590, 690, 697, and/or 790.

Figure 9A:
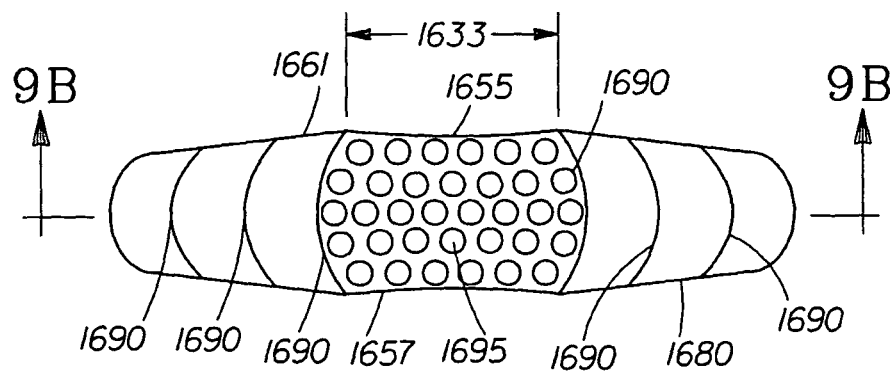
FIGS. 9A-9B are a top view and a side view showing an intermediate member constructed in accordance with the present invention.
Figure 9B:
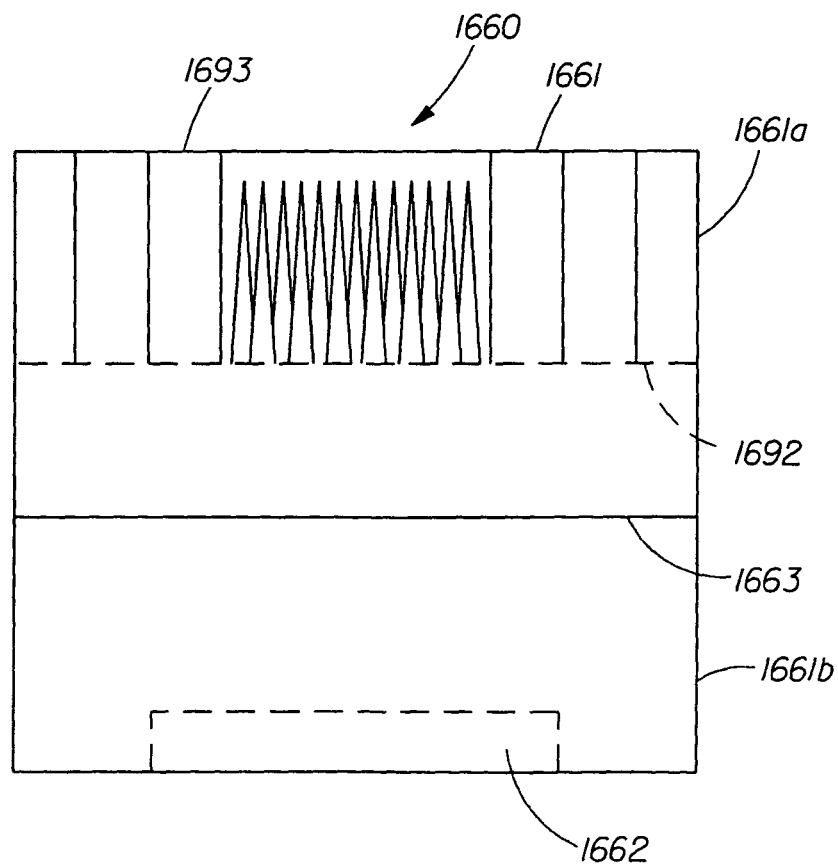
Figure 9C:
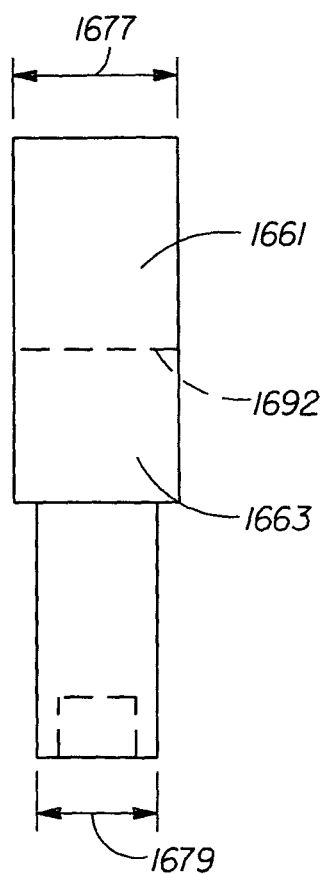
FIG. 9C is an elevation view showing a front face of the intermediate member of FIGS. 9A and 9B.

As shown in FIGS. 9A-9C, another intermediate member 1660 constructed in accordance with the present invention is depicted. The intermediate member 1660 may comprise an intermediate element 1661. The intermediate element 1661 may be constructed as described herein. For example, as shown in FIG. 9A, the intermediate element 1661 may comprise an outer wall 1680 and a plurality of flaps 1690. The flaps 1690 may be curvilinear and may be joined to opposite sides of the outer wall 1680. The flaps 1690 may be configured as described heretofore with regard to the flaps 590, 690, 790, 697, and/or 890.

Additionally, the intermediate member 1660 may comprise a plurality of cilia 1695 extending outward from an intermediate surface 1692 (shown in FIG. 9B). At least some of the cilia 1695 may taper from the intermediate surface 1692 to an outer wall surface 1693 or vice versa, in some embodiments. Embodiments are contemplated where at least some of the projections maintain a substantially constant cross sectional area (within 20%) from the intermediate surface 1692 to the outer wall surface 1693. The plurality of cilia 1695 may be configured similar to the projections 395 discussed previously with regard to FIGS. 3A-3D, in some embodiments.

Referring again to FIG. 9B, in some embodiments, at least some of the cilia 1695 may terminate at the outer wall surface 1693 of the intermediate element 1661. However, embodiments are contemplated where at least some of the cilia 1695 extend and terminate beyond the outer wall surface 1693. The outer wall surface 1693 can be flat, can be convex, can be concave, or a combination thereof. Other suitable outer wall configurations are described herein.

As shown, the intermediate element 1661 may be contoured. Specifically, the intermediate element 1661 may comprise recesses 1655 and 1657. The recesses 1655 and 1657 may be positioned anywhere in the intermediate element 1661. For example, as shown, the recesses 1655 and 1657 are positioned in a mid region 1633 of the intermediate element 1661.

As shown in FIGS. 9B and 9C, the intermediate element 1661 may comprise a notch edge 1663 separating a first portion 1661A from a second portion 1661B of the intermediate element 1661. The first portion 1661A and/or the second portion 1661B may comprise each comprise recesses. However, embodiments are contemplated where the first portion 1661A comprises a recess while the second portion 1661B does not. Additionally, embodiments are contemplated where the second portion 1661B comprise a recess while the first portion 1661A does not.

With regard to FIG. 9C, as shown, in some embodiments, the first portion 1661A may have a first width 1677 which is greater than a second width 1679 of the second portion 1661B. In some embodiments, the first width 1677 may be greater than the second width 1679 by about 1% to by about 90%, or any individual number or any range within this range.

In some embodiments, the second width 1679 can be between about 1 mm and about 10 mm, or any individual number within the range. In some embodiments, the second width 1679 can be greater than about 1 mm, greater than about 2 mm, greater than about 3 mm, greater than about 4 mm, greater than about 5 mm, greater than about 6 mm, greater than about 7 mm, greater than about 8 mm, greater than about 9 mm, and/or less than about 10 mm, less than about 9 mm, less than about 8 mm, less than about 7 mm, less than about 6 mm, less than about 5 mm, less than about 4 mm, less than about 3 mm, or less than about 2 mm. In general, the second width 1679 should be of a sufficient amount such that the intermediate element 1661 does not flop over.

The first width 1677 and/or the second width 1679 correspond to width of the intermediate element 1661 along a transverse axis 2002 (shown in FIG. 1A) of the oral hygiene implement 100 (shown in FIG. 1A). Although not depicted the first portion 1661A may similarly have a greater width than the second portion 1661B along a longitudinal axis 2001 (shown in FIG. 1A) of the oral hygiene implement 100. In such embodiments, the ranges expressed above with regard to the first width 1677 and the second width 1679 are equally applicable. Embodiments are contemplated where the first portion 1661A has a greater width than the second portion 1661B along the transverse axis 2002 (shown in FIG. 1A) and/or the longitudinal axis 2001 (shown in FIG. 1A).

Figure 9D:
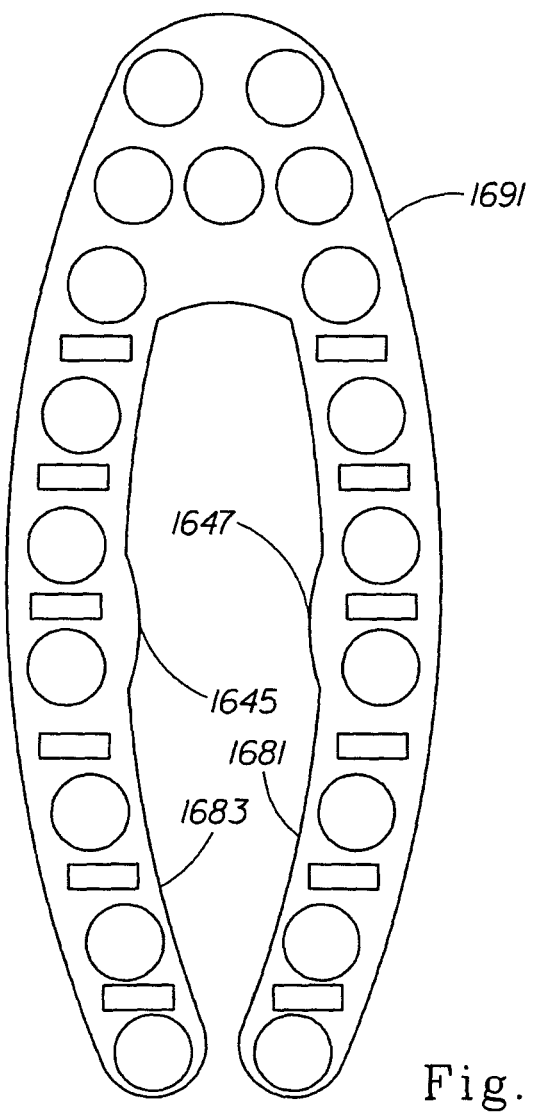
FIG. 9D is a top view showing a cleaning element carrier constructed in accordance with the present invention.

As shown in FIG. 9D, a cleaning element carrier 1691 may comprise a first protrusion 1645 and a second protrusion 1647. These protrusions 1645 and 1647 may engage with the recesses in the second portion 1661B. Embodiments are contemplated where the cleaning element carrier 1691 comprises at least one protrusion. The cleaning element carrier 1691 may be configured in any suitable manner as described herein.

One advantage of the intermediate element 1661 and the cleaning element carrier 1691 is that the intermediate element 1661 and the cleaning element carrier 1691 can form a lock and key type of relationship. For example, the protrusions 1645 and 1647 may engage the recesses in the second portion 1661B of the intermediate element 1661. Because the protrusions 1645 and 1647 engage the recesses of the second portion 1661B, the intermediate element 1661 is provided with some stability in the longitudinal direction.

Another advantage is that the varying widths may provide a spring for the cleaning element carrier 1691. For example, because the protrusions 1645 and 1647 engage recesses in the second portion 1661B, the notch edge 1663 can hinder the movement of the protrusions 1645 and 1647 beyond the second portion 1661B and into the first portion 1661A of the intermediate element 1661. Additionally, if the protrusions 1645 and 1647 engage the notch edge 1663, the notch edge 1663 can serve as a spring creating a force which pushes the cleaning element carrier 1691 toward the body. As such, the intermediate element 1661 and the cleaning element carrier 1691 can form a complimentary relationship and can interactively move/flex together.

Yet another advantage of the intermediate element 1661 is that the real estate of the cleaning element carrier 1691 can be increased. The area of the cleaning element carrier 1691 for the placement of cleaning elements, e.g. bristles, elastomeric elements, fins, etc., is referred to as "real estate" of the cleaning element carrier.

There is a trade off among the available real estate of the cleaning element carrier 1691, the size of the cleaning element carrier 1691, and the size of the intermediate member. For example, in order to maintain a comfortable brushing experience, the width of a cleaning element carrier is desirably reduced. However, the width of the cleaning element carrier also should be wide enough to carry a sufficient amount of cleaning elements. This tradeoff is addressed by the intermediate element 1661.

Because of the varying widths between the second portion 1661B and the first portion 1661A (the first portion 1661A being wider than the second portion 1661B) the cleaning element carrier 1691 can have a reduced width while having an increased amount of real estate. For example, where the inner edges 1681 and 1683 of the cleaning element carrier 1691 engage the second portion 1661B, the width of the cleaning element carrier may be reduced as opposed to the inner edges 1681 and 1683 engaging the first portion 1661A. Additionally, because the first portion 1661A may similarly comprise recesses 1645 and 1647 (shown in FIG. 9A), the amount of real estate on the cleaning element carrier 1691 can be increased. For example, a larger amount of tufting may be utilized at the protrusions 1645 and 1647.

Figure 10A:
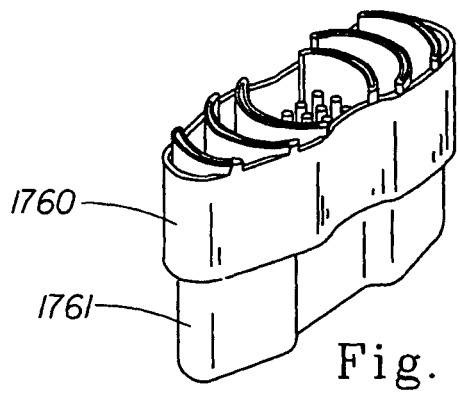
FIGS. 10A-10D are an isometric view, a plan view, a cross sectional view, and a side view each showing another embodiment of an intermediate member constructed in accordance with the present invention.
Figure 10B:
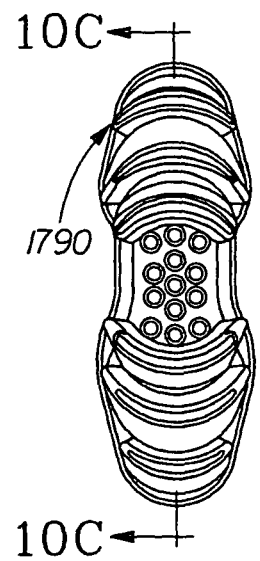
Figure 10C:
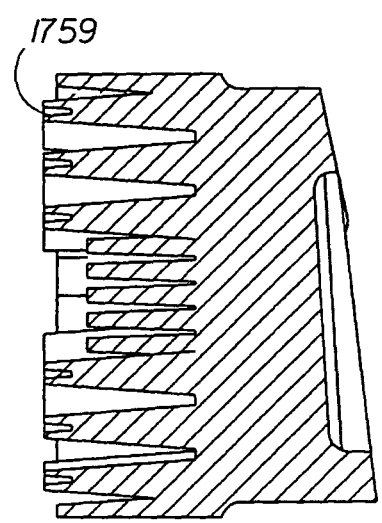
Figure 10D:
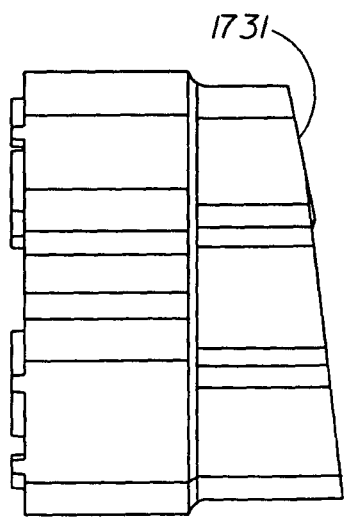
Figure 11A:
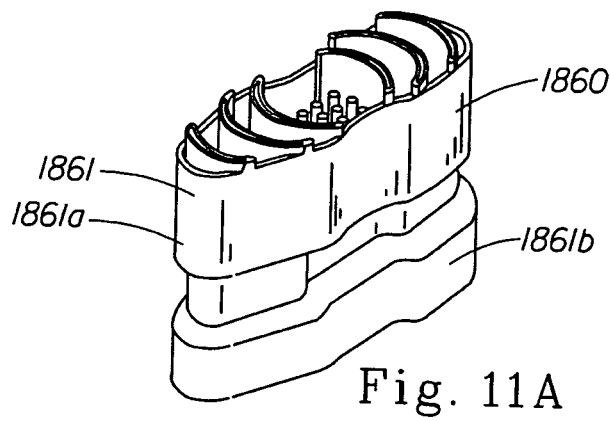
FIGS. 11A-11D are an isometric view, a plan view, a cross sectional view, and a side view each showing another embodiment of an intermediate member constructed in accordance with the present invention.
Figure 11B:
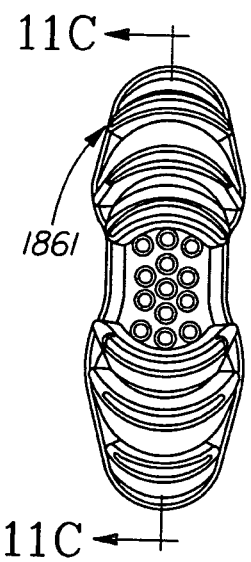
Figure 11C:
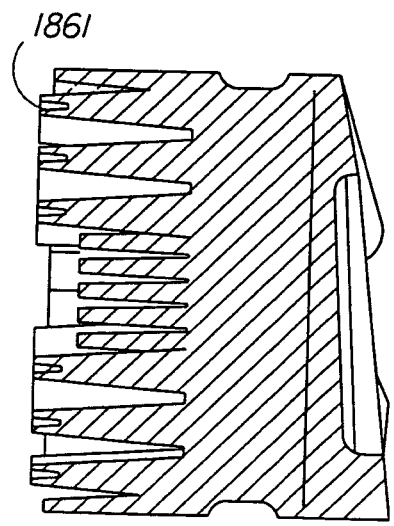
Figure 11D:
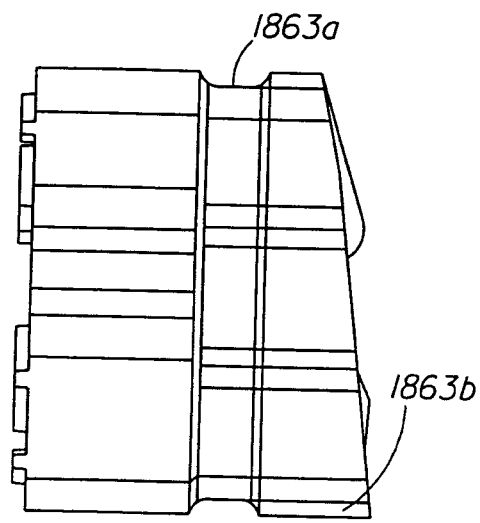

As shown in FIGS. 10A-10D, an intermediate member 1760 constructed in accordance with the present invention is depicted. The intermediate member 1760 may comprise an intermediate element 1761. The intermediate element 1761 may be configured as described herein with regard to the intermediate element 1661. However, flaps 1790 may comprise cavities 1759 at their extremeties. Embodiments are contemplated where at least one flap 1790 comprises a cavity 1759. The flaps 1790 may be configured as described heretofore with regard to the flaps 590, 690, 790, 697, 890, and/or 1691. Additionally, as shown in FIG. 10D, the intermediate element 1761 may comprise a beveled bottom edge 1731.

As shown in FIGS. 11A-11D, an intermediate member 1860 constructed in accordance with the present invention is depicted. The intermediate member 1860 may comprise an intermediate element 1861. The intermediate element 1861 may comprise a first portion 1861A and a second portion 1861B. The first portion 1861A and the second portion 1861B may be configured similarly to the first portion 1661A and the second portion 1661B as described above. However, the second portion 1861B may be configured such that a first section 1863A of the second portion 1861B has a reduced width compared to the first portion 1861A while a second section 1863B of the second portion 1861B has a width which is similar to that of the first portion 1861A. The ratios of widths discussed heretofore with regard to the first portion 1661A and the second portion 1661B are equally applicable to the first portion 1861A, the second portion 1861B, the first section 1863A and/or the second section 1863B.

One advantage of this intermediate element 1861 is that the interface between the first section 1863A and the first portion 1861A and the interface between the first section 1863A and the second section 1863B can provide spring like forces to a cleaning element carrier. For example, the interface between the first section 1863A and the first portion 1861A can provide a force which pushes a cleaning element carrier toward a body when an upward force is applied to the cleaning element carrier. In contrast, the interface between the first section 1863A and the second section 1863B can provide a force which pushes the cleaning element carrier upward away from the body when the cleaning element carrier is depressed.

Figure 12:
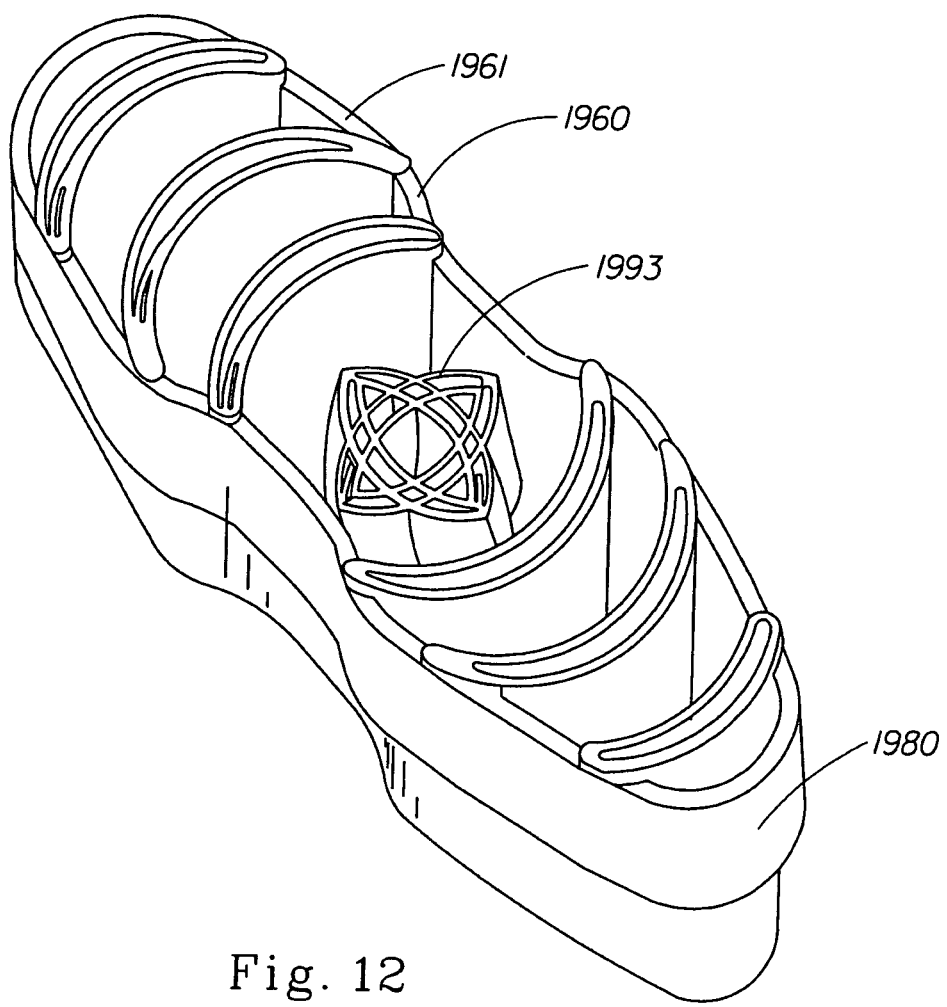
FIG. 12 is an isometric view showing another embodiment of an intermediate member constructed in accordance with the present invention.
Figure 13:
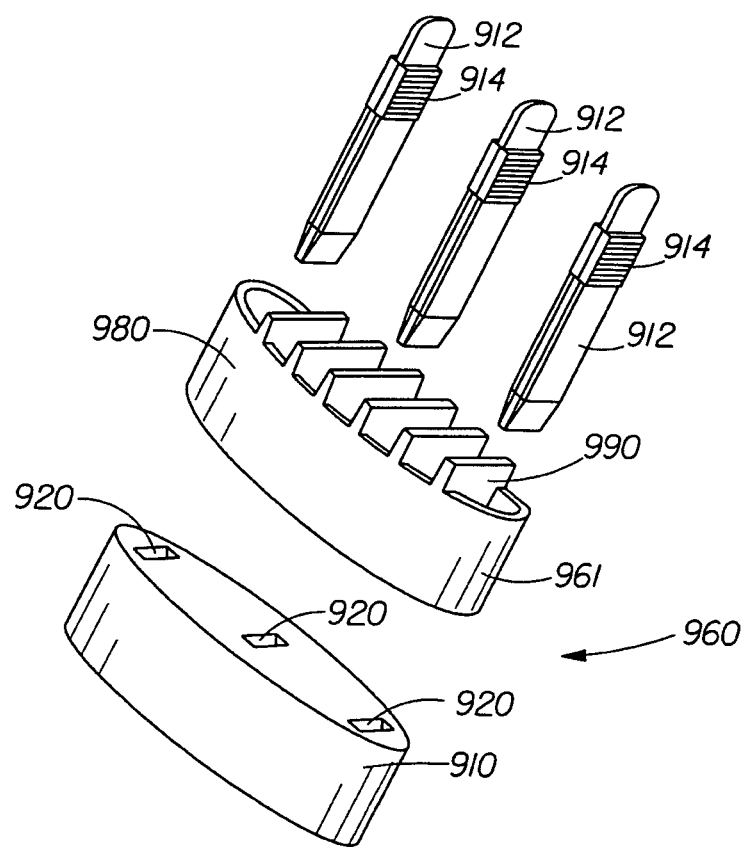
FIG. 13 is an exploded isometric view showing another embodiment of an intermediate member constructed in accordance with the present invention.

Another embodiment of an intermediate member constructed in accordance with the present invention is depicted in FIG. 12. As shown, an intermediate member 1960 may comprise an intermediate element 1961. The intermediate element 1961 may be constructed as discussed herein with regard to the intermediate elements 1661, 1761, and/or 1861. Additionally, the intermediate element 1961 may comprise a four-pointed star 1993 disposed within an outer wall 1980 of the intermediate element 1961. The star 1993 may terminate in a plane beyond the outer wall, may terminate in the same plane as the outer wall, or may terminate in a plane within the outer wall. The star 1993 may act as a reservoir to hold oral compositions.

As stated previously, intermediate members constructed in accordance with the present invention may comprise a plurality of discrete members, elements, etc. For example, referring now to FIG. 13, an intermediate member 960 constructed in accordance with the present invention may comprise an intermediate element 961, fins 912, and an intermediate base 910. Similar to the intermediate elements 461, 561, and 661, 761, and 861, the intermediate element 961 may comprise an outer wall 980 and a plurality of flaps 990. The flaps 990 may be configured in any suitable manner, for example, as discussed heretofore.

The intermediate member 960 may further comprise the plurality of fins 912 which may be received in the receptacles created by the flaps 990. The fins 912 may be integrally formed with the intermediate element 961. Alternatively, the fins 912 may comprise discrete elements which are separately joined to a body of the toothbrush. For example, in the embodiment shown, the intermediate element 961 may be attached to an intermediate base 910. The intermediate base 910 may include a plurality of openings 920 adapted to receive the fins 912 therein.

The fins 912 may be snap fitted into the openings 920. The fins 912 may be adhesively attached to the intermediate base 910. The fins 912 may be attached to the intermediate element 961, the intermediate base 910, and/or the body via any suitable method. Some suitable methods are disclosed in U.S. Pat. No. 6,553,604 and U.S. Patent Application Publication No. 2005/0235439.

As shown, in some embodiments, the fins 912 may comprise ridges 914. The ridges 914 may be integrally formed with the fins 912. Alternatively, the ridges 914 may be formed from a second material which is different from a material utilized for the fins 912. In some embodiments, the ridges 914 may be formed from the same material as the fins 912, e.g. thermoplastic elastomers. Suitable materials, processes, and design for the ridges 914 and the fins 912 are further described in U.S. Patent Application Publication No. 2005/0235439.

Figure 14:
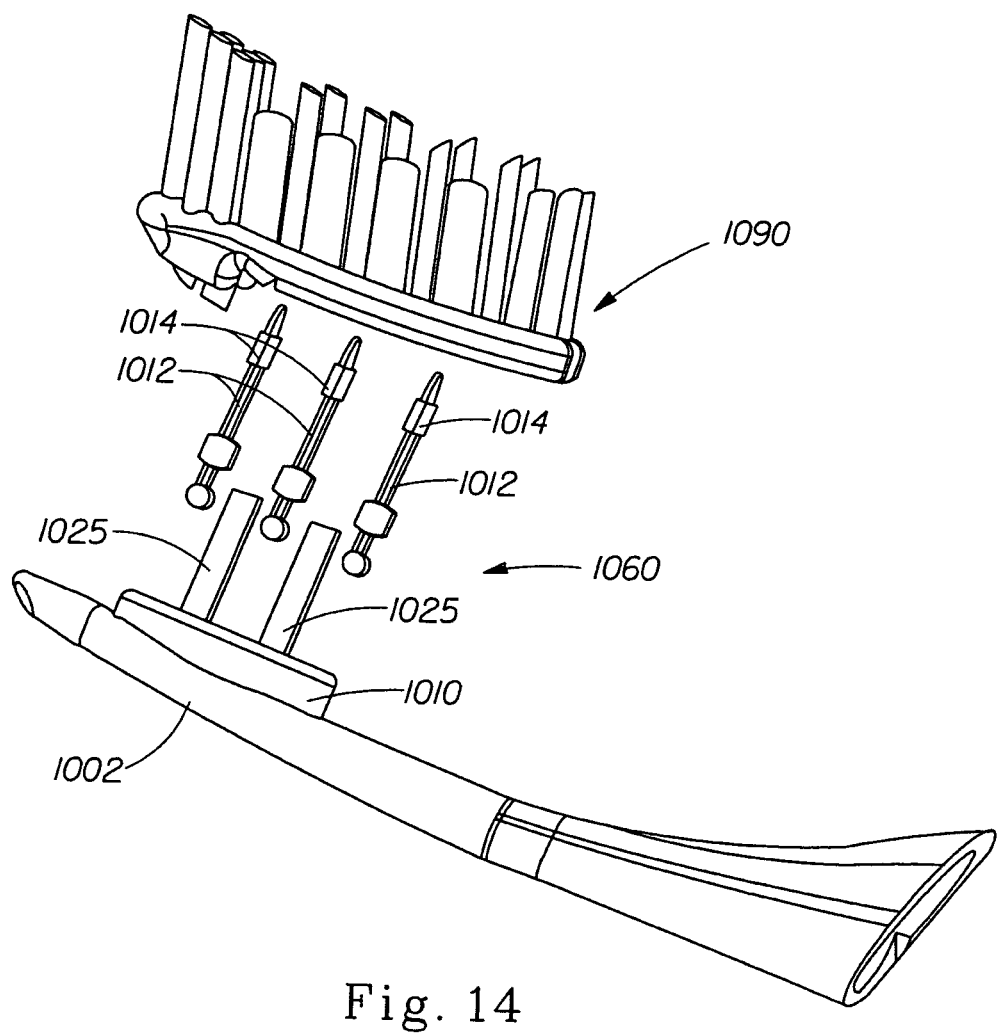
FIG. 14 is an exploded side view showing another embodiment of an intermediate member constructed in accordance with the present invention.

As shown in FIG. 14, another example of an intermediate member comprising a plurality of discrete parts is provided. As shown, an intermediate member 1060 may comprise an intermediate base 1010, cleaning elements 1025, and a plurality of fins 1012. The intermediate base 1010 may be joined to the body 1002 by any suitable means. Some examples of suitable methods include adhesives, welding, injection molding, and the like. Similarly, the plurality of fins 1012 may be joined to the intermediate base 1010, and/or a body 1002 of the toothbrush via any suitable method. Some examples of suitable methods are disclosed above with regard to the fins 912 (shown in FIG. 13).

Additionally, the plurality of fins 1012 may comprise ridges 1014. The ridges 1014 may be configured as described above with regard to the ridges 914 (shown in FIG. 13).

Figure 15B:
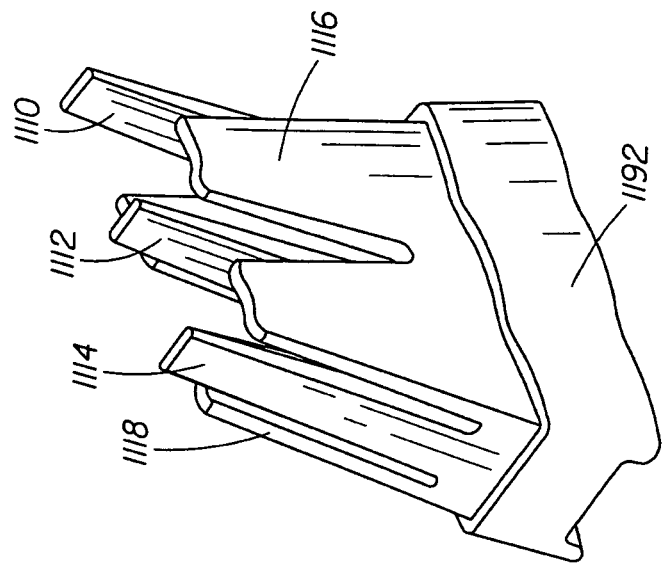
FIGS. 15A and 15B are perspective views showing another embodiment of an intermediate member constructed in accordance with the present invention.
Figure 15A:
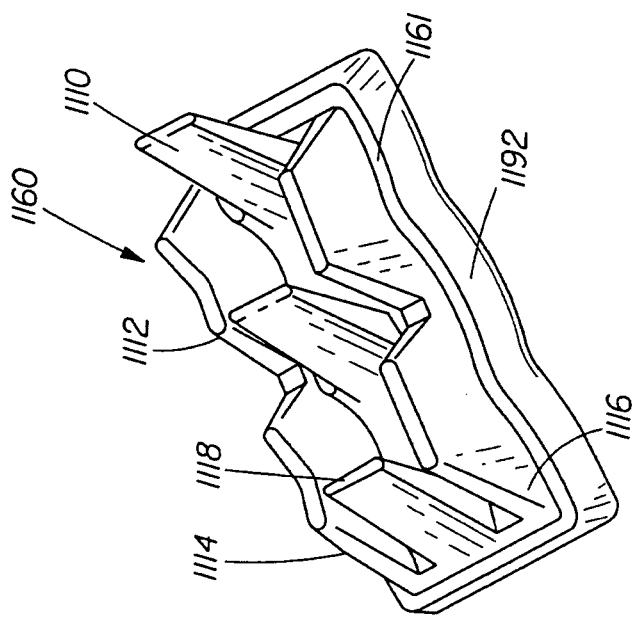

Another example of a suitable intermediate member constructed in accordance with the present invention is shown in FIGS. 15A-15E. As shown in FIG. 15A, an intermediate member 1160 may comprise an intermediate element 1161, a base portion 1192, and a secondary cleaning surface 1193. The intermediate element 1161 may comprise a pair of side walls 1116 and 1118 and a flap, e.g. 1110, 1112, and 1114. As shown in FIGS. 15A and 15B, the flaps 1110, 1112, and/or 1114 may be angled with respect to the base portion 1192. Any suitable angle may be utilized. Some examples of suitable angles are described in U.S. Pat. No. 6,308,367. The angled flaps may promote the wiping action of the flaps and promote the interdental cleaning provided by the angled flaps. Although the intermediate member 1160 shown in FIGS. 15A-15E comprises only three flaps, embodiments are contemplated where the intermediate member 1160 comprises at least one, and embodiments are contemplated where the intermediate member 1160 comprises more than three.

Additionally, as shown, in some embodiments, the side walls 1116 and/or 1118 may be contoured. For example, in one specific embodiment, the side wall 1116 and/or the side wall 1118 may have a wavy outer surface in either a longitudinal or lateral direction, i.e. 1194 and 1195, respectively (shown in FIG. 15C).

Figure 15C:
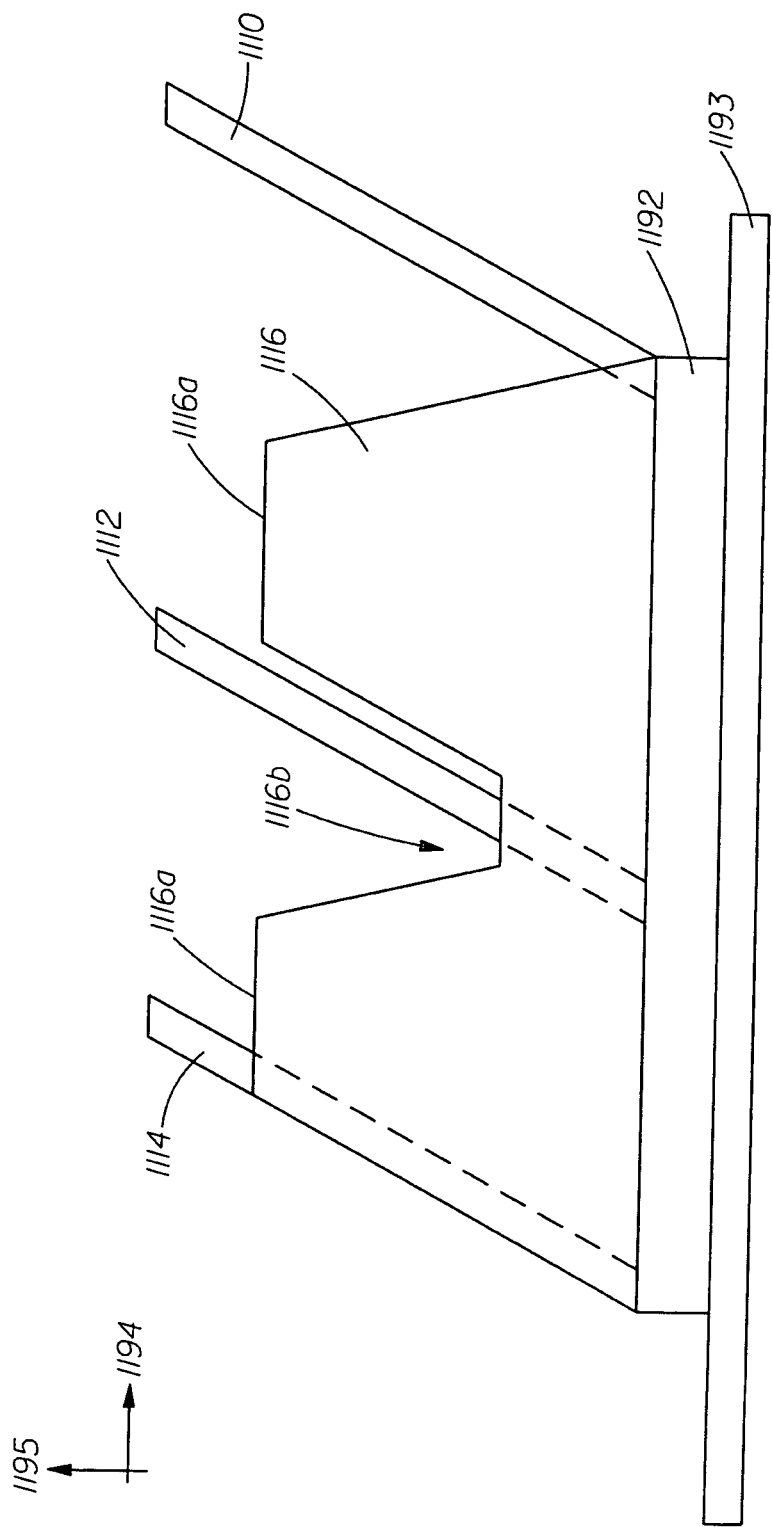
FIGS. 15C and 15D are elevation views showing the intermediate member of FIG. 15A.

As shown in FIG. 15C, the side wall 1116, side wall 1118, and/or flaps 1110, 1112, and 1114, may be joined to the base portion 1192 and extend outward therefrom. The side walls 1116, 1118, and/or flaps 1110, 1112, and 1114, may be integrally formed with the base portion 1192 or may be attached to the base portion 1192 as a unitary discrete element or a plurality of discrete elements.

In some embodiments, the base portion 1192 can be joined to the secondary cleaning surface 1193. Similarly, the base portion 1192 can be integrally formed with the secondary cleaning surface 1193 or attached as a unitary discrete element or a plurality of discrete elements.

As shown in FIG. 15C, the side wall 1116 and/or the side wall 1118 may comprise peaks 1116A and valleys 1116B. The side walls 1116 and 1118 can provide a benefit of maintaining a reservoir for a dentifrice or other oral composition. Additionally, the intermediate member 1160 may be more flexible because of the valley 1116B between the peaks 1116A. As shown, in some embodiments, the flaps 1110, 1112, and/or 1114 may extend outward beyond the peaks 1116A of the side wall 1116.

Figure 15D:
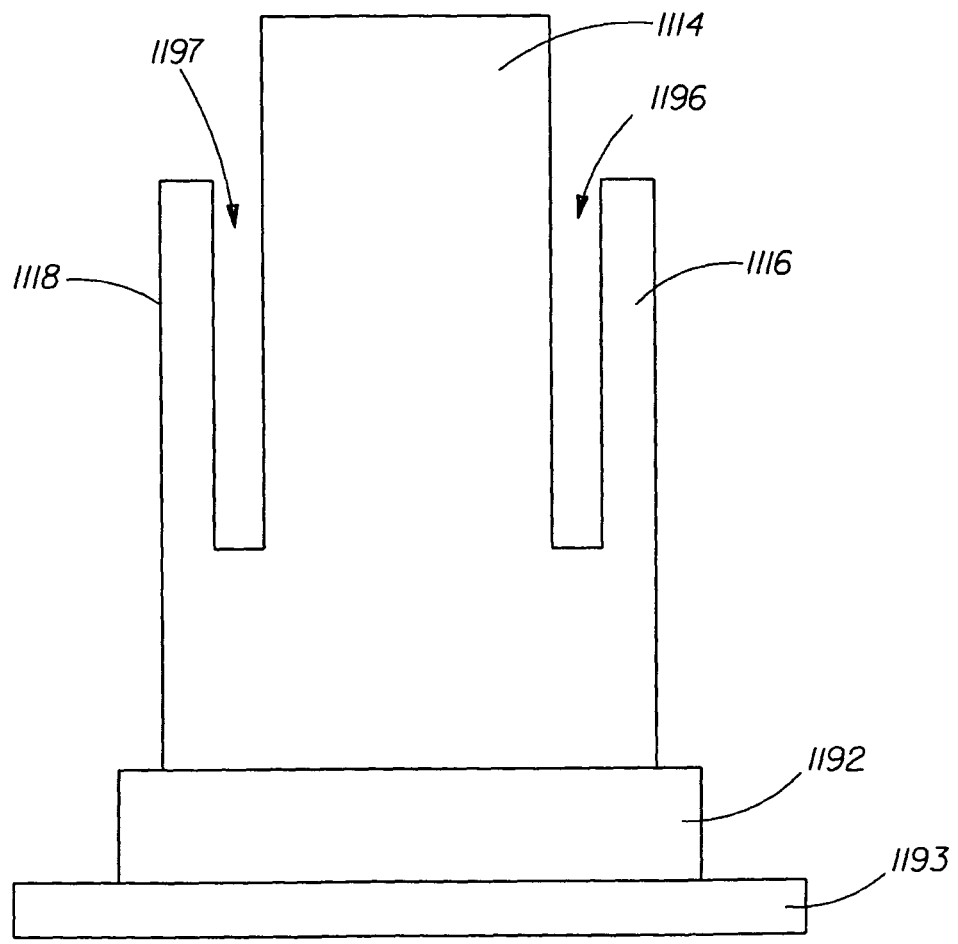

As shown in FIG. 15D, in addition to the valleys 1116B (shown in FIG. 15C), the intermediate element 1161 may further comprise gaps 1196 and 1197 between the side wall 1116 and the flap 1114 and the side wall 1118 and the flap 1114, respectively. The flaps 1110 and/or 1112 may be configured similarly. The addition of the gaps 1196 and 1197 allow the intermediate element 1161 to be more flexible thereby increasing the comfort to the user.

Figure 15E:
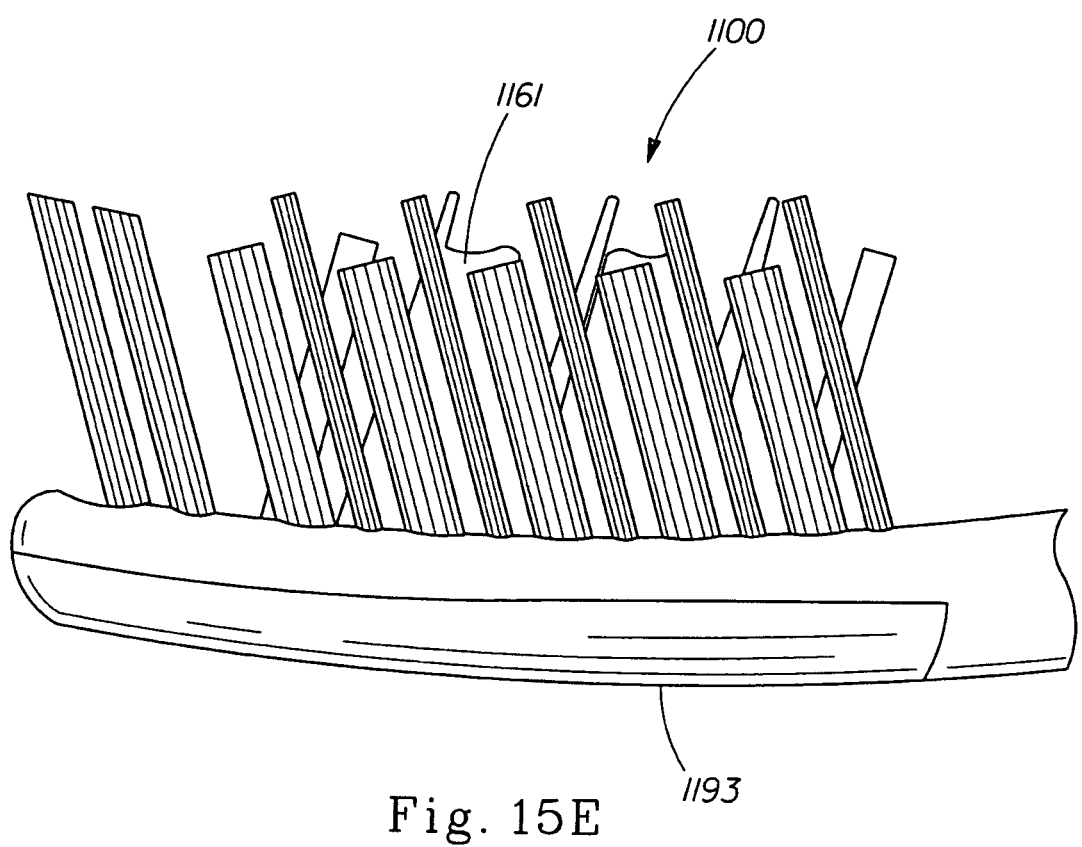
FIG. 15E is an elevation view showing the intermediate member of FIG. 15A incorporated into a toothbrush.

As shown in FIG. 15E, the intermediate member 1160 may be incorporated into an oral hygiene implement such as a toothbrush 1100. For example, as shown, the secondary cleaning surface 1193 may be disposed on the backside of the toothbrush while the intermediate element 1161 extends in the same general direction as the bristles on the opposite side of the toothbrush.

Also, embodiments are contemplated where the intermediate members are inserted into an opening in a toothbrush body. For example, the intermediate member 1160 may be inserted an opening in the toothbrush 1100 from a backside facing surface of the toothbrush 1100. The base portion 1192 of the intermediate member 1160 can secure the intermediate member 1160 in the opening of the toothbrush 1100.

In some embodiments, intermediate members may comprise a combination of elastomeric components and bristles. In some embodiments, the intermediate member may comprise only bristles. Examples of such embodiments are shown with regard to FIGS. 16A-17C.

Figure 16A:
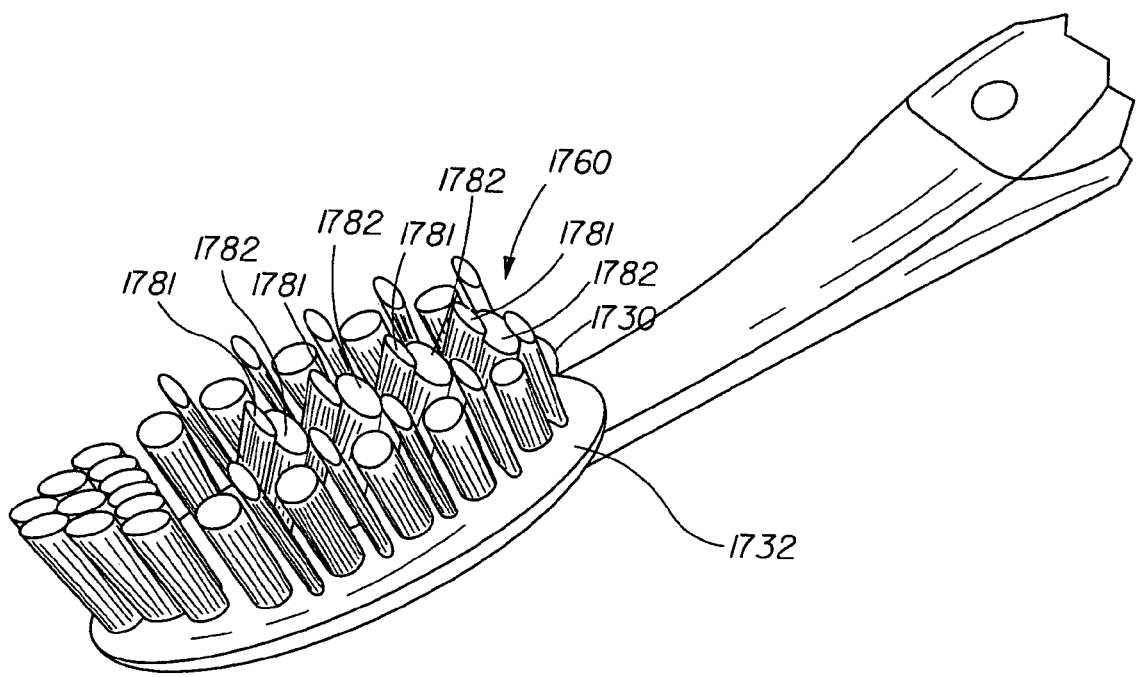
FIGS. 16A-16C are various views showing another embodiment of a brush constructed in accordance with the present invention.
Figures 16B, 16C:
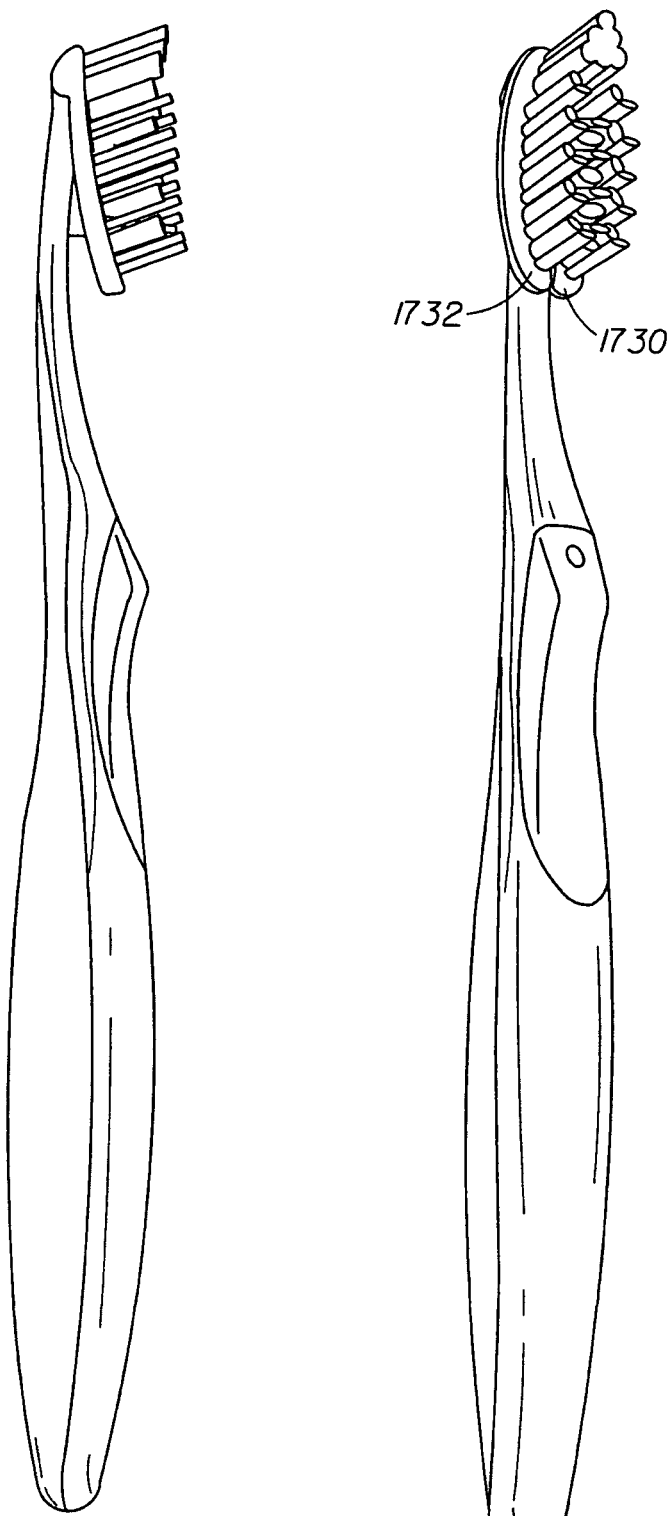

As shown in FIGS. 16A-16C, the intermediate member 1760 may comprise a plurality of bristle tufts 1781 and 1782. The bristle tufts 1781 and 1782 may be arranged such that they extend through an intermediate opening between a first carrier member 1730 and a second carrier member 1732. The bristle tufts 1781 may be configured in any suitable manner. For example, the bristle tufts 1781 and 1782 may be configured as described in U.S. Pat. No. 6,308,367.

Figure 17A:
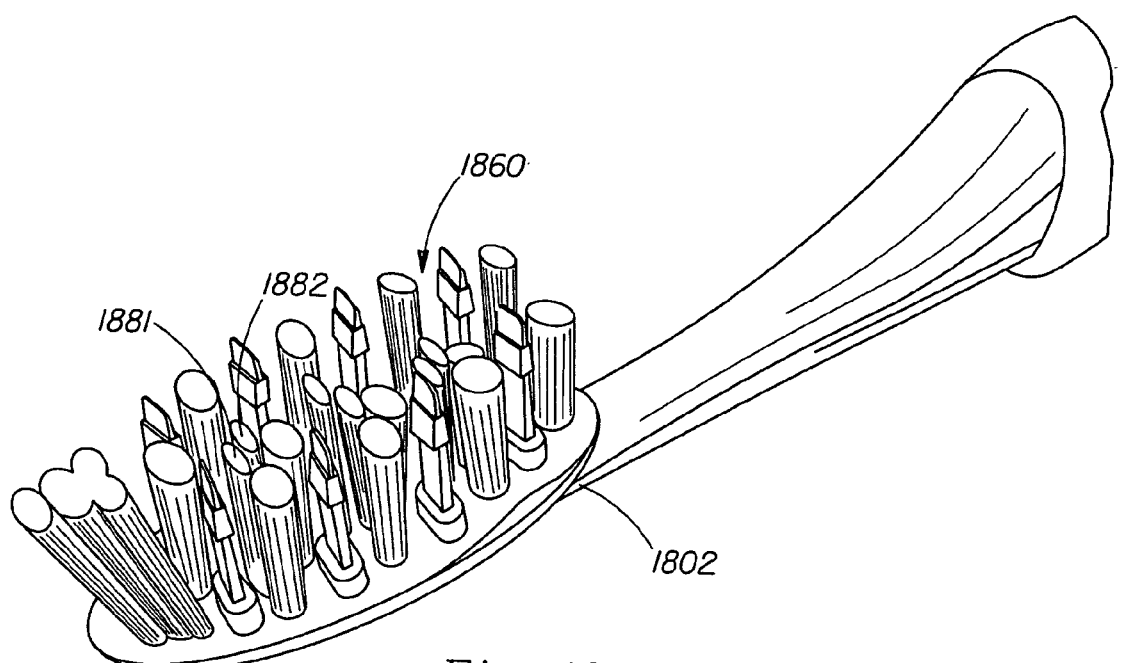
FIGS. 17A-17C are various views showing another embodiment of a brush constructed in accordance with the present invention.
Figures 17B, 17C:
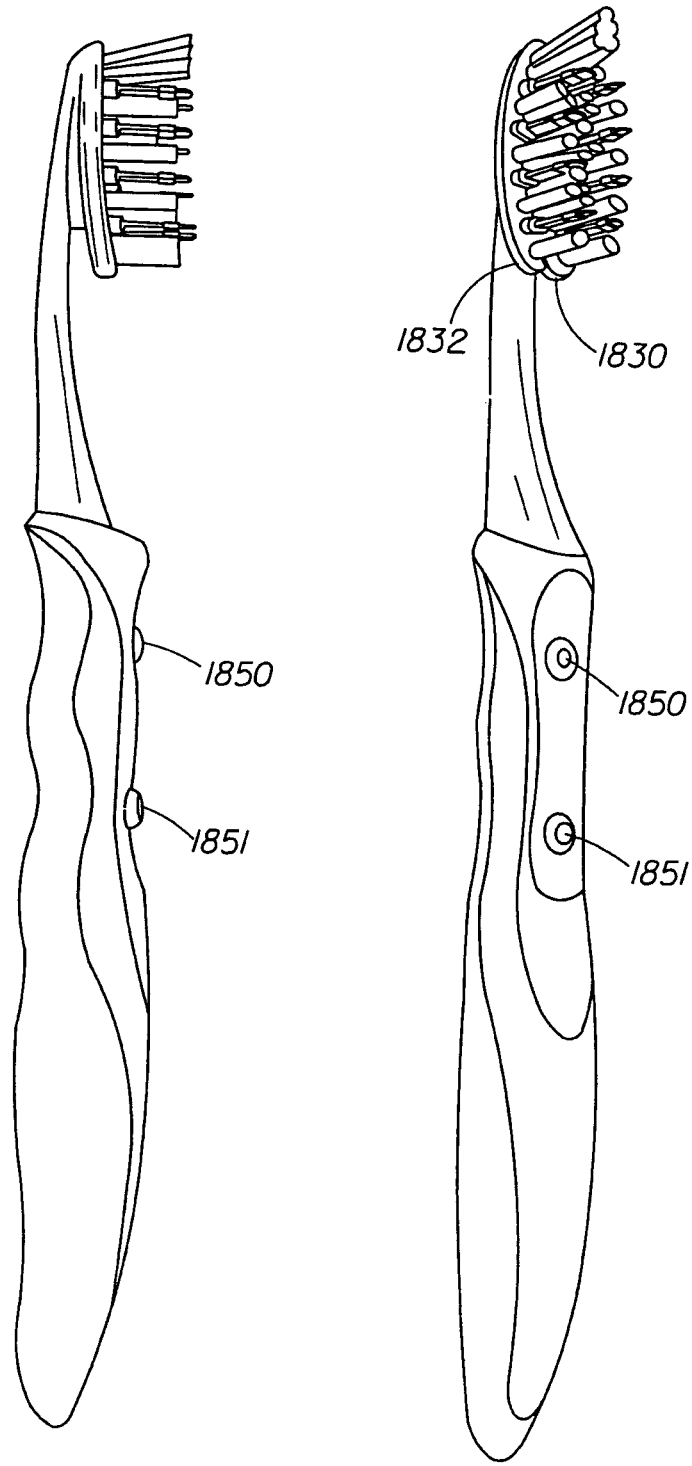

As shown in FIGS. 17A-17C, the intermediate member 1860 may comprise a plurality of bristle tufts 1881 and 1882. In this embodiment, the bristles 1881 and 1882 may be disposed generally perpendicular to the body 1802 of the brush.

Additionally, as shown in FIGS. 17A-17C, a brush constructed in accordance with the present invention may comprise a powered element, e.g. a vibratory element, an LED, a sensor, combinations, and the like. The powered element may be turned on/off via a bi-stable switch having an on button 1850 and an off button 1851. Vibratory elements, LED's, and sensors are well known and may be positioned in any suitable location with respect to the brush, e.g. the handle, the neck, the head, etc.

The intermediate members of the present invention may be configured in a number of different manners. For example, as discussed herein, in some embodiments, intermediate members may be attached to the body via attachment cavities and attachment keys. Additionally, embodiments, are contemplated where the intermediate members are attached to the body and/or the suspension layer. For example, the intermediate member may be cantilevered such that an outward most portion of the intermediate member is unattached to the body. As another example, the intermediate member may be cantilevered such that an inward most portion of the intermediate member is unattached to the body.

The cleaning element fields, e.g. 60, 70, 80, and 90 (all shown in FIG. 1B) and cleaning elements 1025 of the present invention may comprise a wide variety of materials and may have a number of different configurations. Any suitable material and/or any suitable configuration may be utilized. Additionally, it should be noted that the cleaning elements may comprise any suitable cleaning element and/or may comprise elements which are utilized for massaging gums, cleaning the tongue, providing chemistry to an area of the oral cavity, e.g. antimicrobial agents, malodor agents, flavor agents, anti-plaque agents, anti-gingivitis agents, whitening agents, or the like.

For example, in some embodiments, the cleaning element fields 60, 70, 80, 90, the cleaning elements 1025, and/or the intermediate member, may comprise tufts. The tufts may comprise a plurality of individual filaments which are securely attached to a cleaning element carrier. Such filaments may be polymeric and may include polyamide or polyester. The longitudinal and cross sectional dimensions of the filaments of the invention and the profile of the filament ends can vary. Additionally, the stiffness, resiliency and shape of the filament end can vary. Some examples of suitable dimensions include a length between about 3 cm to about 6 cm, or any individual number within the range. Additionally, the filaments may include a substantially uniform cross-sectional dimension of between about 100 to about 350 microns, or any individual number within the range. The tips of the filaments may be any suitable shape, examples of which include a smooth tip, a rounded tip, a pointed tip. In some embodiments, the filaments may include a dye which indicates wear of the filaments as described in U.S. Pat. No. 4,802,255. Some examples of suitable filaments for use with the brush of the present invention are described in U.S. Pat. No. 6,199,242. In some embodiments, the cleaning elements may comprise fins as described heretofore. For example, in some embodiments, the cleaning element fields may comprise a combination of fins and tufts.

Additionally, at least a portion of some of the cleaning element fields 60, 70, 80, 90, and/or cleaning elements 1025 may be attached to a cleaning element carrier at an angle. Such orientations are described in U.S. Pat. No. 6,308,367. Also, any suitable method may be utilized to attach the tufts to the cleaning element carrier and/or the body.

The suspension layer and/or the intermediate members, intermediate elements, of the present invention may comprise any suitable material. Some suitable examples of material include a thermoplastic elastomer (TPE), thermoplastic urethane (TPU), rubber, silicone, foam, combinations thereof, or the like.

Additionally, the intermediate members of the present invention may comprise any suitable material. Some examples include those described above with regard to the suspension layer. Also, the intermediate members, as discussed previously, may comprise tufts of filaments. The intermediate members of the present invention may comprise any suitable combination of tufts, fins, intermediate elements, etc.

The oral hygiene implement body of the present invention may be formed from a wide variety of materials. Some suitable examples of materials which can be utilized to construct the body include a polyethylene (PE), polypropylene (PP), polyethyleneterapthalate (PET), acrylonitrile-butadiene-styrene (ABS), and styrene-acrylonitrile (SAN), PP and TPE blends, acetal (POM), nylon (PA), modified polyphenylene oxid (PPO), polyester (PBT), polycarbonate (PC), high impact polystyrene (HIPS), isoplast and other TPU materials, the like, and suitable combinations thereof.

The cleaning element carrier, the first carrier member and/or the second carrier member may be formed from any suitable material. Some examples include those described above with regard to the body. Additionally, in some embodiments, the first carrier member and/or the second carrier member may comprise the same material or may comprise different materials. Similarly, in some embodiments, the first carrier member and/or the second carrier member may comprise different materials from those utilized in the body.

The present invention may be utilized in manual toothbrushes where the cleaning motion is supplied completely by a user. However, embodiments are contemplated where the present invention comprises a manual toothbrush which supplements the user's motions with a vibration device as described in U.S. Patent Application Publication No. 2003/0162145. Moreover, embodiments are contemplated where the present invention includes a power toothbrush. A power toothbrush is one where the toothbrush provides the majority of the cleaning motion. The user may manipulate the power toothbrush to ensure that the power toothbrush contacts the desired oral surfaces. In such embodiments, the cleaning element fields, e.g. 60, 70, 80, and 90 (all shown in FIG. 1B), cleaning elements 1025 (shown in FIG. 10), and/or the intermediate elements described herein, may be driven in a variety of motions. Some examples of such suitable motions are described in U.S. Patent Application Publication No. 2003/0084527. Also, embodiments are contemplated where the present invention includes a replaceable brush head for a power and/or a manual toothbrush.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

The following text sets forth a broad description of numerous different embodiments of the present invention. The description is to be construed as exemplary only and does not describe every possible embodiment since describing every possible embodiment would be impractical, if not impossible, and it will be understood that any feature, characteristic, component, composition, ingredient, product, step or methodology described herein can be combined with or substituted for, in whole or part, any other feature, characteristic, component, composition, ingredient product, step or methodology described herein. Numerous alternative embodiments could be implemented, using either current technology or technology developed after the filing date of this patent, which would still fall within the scope of the claims.

What is claimed is:

1. An oral hygiene implement including a body having a distal end and a proximal end, the oral hygiene implement further comprising a cleaning or gum massaging element carrier, the gum massaging element carrier comprising a first carrier member having a first proximal area and a first distal area; and a second carrier member having a second proximal area and a second distal area, wherein the first proximal area and the second proximal area are attached to the body such that the first carrier member and the second carrier member extend toward the body, wherein the first carrier member and the second carrier member are configured such that the first distal area and the second distal area are unattached to the body and the first carrier member and second carrier member defining an intermediate opening there between and the oral hygiene implement further comprising an elastomeric member attached to the body and extending through the intermediate opening.

2. The oral hygiene implement of claim 1 wherein the elastomeric member comprises a continuous outer wall forming an outer wall surface and a plurality of flaps extending from an intermediate surface, wherein at least one of the plurality of flaps are taller than the outer wall surface.

3. The oral hygiene implement of claim 2, wherein the elastomeric member further comprises a plurality of bristles extending through the intermediate opening.

4. The oral hygiene implement of claim 2 wherein the elastomeric member comprises a base portion, a pair of side walls attached to the base portion, each side wall comprising a peak and a valley, a plurality of flaps attached to the base portion and disposed between the pair of side walls, wherein the side walls and the flaps form at least one reservoir.

5. The oral hygiene implement of claim 1 wherein the elastomeric member supports cleaning elements.

6. An oral hygiene implement having a longitudinal axis, a lateral axis, and a transverse axis, the oral hygiene implement further comprising:
   a body;
   a first carrier member having a first proximal area and a first distal area; and
   a second carrier member having a second proximal area and a second distal area,
wherein the first proximal area and the second proximal area are attached to the body such that the first carrier member and the second carrier member extend toward the body, wherein the first carrier member and the second carrier member are configured such that the first distal area and the second distal area are unattached to the body and can flex independently of one another.

7. The oral hygiene implement of claim 6 wherein the first distal area, second distal area, or both can flex in a direction generally parallel to the transverse axis.

8. The oral hygiene implement of claim 6 wherein the first distal, second distal area, or both can flex in a direction generally parallel to the lateral axis.

9. The oral hygiene implement of claim 6 wherein at least one of the first distal area or the second distal area can flex in a direction generally parallel to the transverse axis and can flex in a direction generally parallel to the lateral axis.

10. The oral hygiene implement of claim 6, wherein the first carrier member and the second carrier member form an intermediate opening therebetween, wherein the oral hygiene implement further comprises an intermediate member attached to the body and extending through the intermediate opening.

11. An oral hygiene implement including a body having a distal end and a proximal end, the oral hygiene implement further comprising:
   a cleaning element carrier, the cleaning element carrier comprising a first carrier member having a first proximal area and a first distal area and a second carrier member having a second proximal area and a second distal area, wherein the first proximal area and the second proximal area are attached to the body such that the first carrier member and the second carrier member extend toward the body, wherein the first carrier member and the second carrier member are configured such that the first distal area and the second distal area are unattached to the body, wherein the first and second distal areas are disposed inboard of the first and second proximal areas; and
   a bending element disposed between the first proximal area and the first distal area and the second proximal area and the second distal area thereby allowing the first and second distal areas to move while the first and second proximal areas stay fixed.

12. The oral hygiene implement of claim 11 wherein the bending element is a weakened area.

13. The oral hygiene implement of claim 11 wherein the cleaning element carrier is made from a first material and the bending element comprises a second material, and wherein the second material is different from the first material.

14. The oral hygiene implement of claim 11 wherein the bending element is integral with the cleaning element carrier.

15. The oral hygiene implement of claim 11 wherein the bending element is discrete and is attached to the cleaning element carrier.

16. An intermediate member for use in the oral hygiene implement of claim 1, the intermediate member comprising:
   a base portion;
   a pair of side walls attached to the base portion, each side wall comprising a peak and a valley; and
   a plurality of flaps attached to the base portion and disposed between the pair of side walls, wherein the side walls and the flaps form at least one reservoir, and wherein the flaps and the side walls are separated by a gap.

17. The intermediate member of claim 16 wherein the flaps are angled with respect to the base portion.

18. The intermediate member of claim 16 wherein the side walls are wavy.

19. The intermediate member of claim 16 wherein the intermediate member further comprises a secondary cleaning surface attached to a side of the base portion opposite the side walls and flaps.

20. An oral hygiene implement comprising the intermediate member of claim 19.

* * * * *